United States Patent
Verneris et al.

(10) Patent No.: US 9,862,928 B2
(45) Date of Patent: Jan. 9, 2018

(54) GENERATION OF NATURAL KILLER CELLS AND LYMPHOID TISSUE INDUCER-LIKE (LTI-LIKE) NK-22 CELLS

(75) Inventors: Michael Verneris, Minnetonka, MN (US); Jeff Miller, North Oaks, MN (US); Bruce Blazar, Golden Valley, MN (US); Yong-Oon Ahn, Falcon Heights, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 524 days.

(21) Appl. No.: 13/991,370

(22) PCT Filed: Dec. 2, 2011

(86) PCT No.: PCT/US2011/063098
§ 371 (c)(1),
(2), (4) Date: Nov. 26, 2013

(87) PCT Pub. No.: WO2012/075412
PCT Pub. Date: Jun. 7, 2012

(65) Prior Publication Data
US 2014/0072545 A1    Mar. 13, 2014

Related U.S. Application Data

(60) Provisional application No. 61/419,689, filed on Dec. 3, 2010.

(51) Int. Cl.
*C12N 5/0783* (2010.01)

(52) U.S. Cl.
CPC ...... *C12N 5/0646* (2013.01); *C12N 2501/125* (2013.01); *C12N 2501/2303* (2013.01); *C12N 2501/2307* (2013.01); *C12N 2501/2315* (2013.01); *C12N 2501/26* (2013.01); *C12N 2502/13* (2013.01); *C12N 2506/11* (2013.01)

(58) Field of Classification Search
None
See application file for complete search history.

(56) References Cited

U.S. PATENT DOCUMENTS

| | | | |
|---|---|---|---|
| 5,641,670 | A | 6/1997 | Treco et al. |
| 6,361,972 | B1 | 3/2002 | Harrington et al. |
| 6,410,266 | B1 | 6/2002 | Harrington et al. |
| 6,524,818 | B1 | 2/2003 | Harrington et al. |
| 6,524,824 | B1 | 2/2003 | Sherf et al. |
| 6,541,221 | B1 | 4/2003 | Harrington et al. |
| 6,602,686 | B1 | 8/2003 | Harrington et al. |
| 6,623,958 | B1 | 9/2003 | Harrington et al. |

FOREIGN PATENT DOCUMENTS

| | | |
|---|---|---|
| WO | WO-2006102209 A2 | 9/2006 |
| WO | WO-2012075412 A1 | 6/2012 |

OTHER PUBLICATIONS

Tang et al (Oral presentation, Dec. 5, 2010).*
Grzywacz et al (Blood, 2006, 108(12): 3824-3833).*
Sigma Aldrich, 2015.*
Cella et al (PNAS, Jun. 15, 2010, 107(24): 10961-10966).*
"International Application Serial No. PCT/US2011/063098, International Preliminary Report on Patentability dated Jun. 13, 2013", 9 pgs.
Bachanova, Veronika, et al., "Activated Notch Supports Development of cytokine Producing NK Cells Which Are Hyporesponsive and Fail to acquire NK Cell Effector Functions", *Biology of Blood and Marrow Transplant*, 15(2), (2009), 183-194.
Cichocki, Frank, et al,, "In Vitro Development of Human Killer-Immunoglobulin Receptor-Positive NK Cells", *Natural Killer Cell Protocols, Methods Mol. Biol.*, 612, Campbell, K. S., (ed.), (2010), 15-26.
Crellin, Natasha K., et al., "Human NKp44+IL-22+ cells and LTi-like cells constitute a stable RORC+ lineage distinct from conventional natural killer cells", *J. Exp. Med.*, 207(2), (2010), 281-290.
McCullar, Valarie, et al., "Mouse fetal and embryonic liver cells differentiate human umbilical cord blood progenitors into CD56-negative natural killer cell precursors in the absence of interleukin-15", *Exp. Hematol.*, 36(5), (2008), 598-608.
"International Application Serial No. PCT/US2011/063098, Search Report dated May 9, 2012", 6 pgs.
"International Application Serial No. PCT/US2011/063098, Written Opinion dated May 9, 2012", 7 pgs.
Cella, Marina, et al., "A Human Natural Killer Cell Subset Provides an Innate Source of IL-22 for Mucosal Immunity", Nature, vol. 457, No. 7230, (Feb. 5, 2009), 722-725.
Colonna, Marco, "Interleukin-22-Producing Natural Killer Cells and Lymphoid Tissue Inducer-like Cells in Mucosal Immunity", Immunity, vol. 31, No. 1, (Jul. 2009), 15-23.
Freud, Aharon G, et al., "A Human CD34 (+) Subset Resides in Lymph Nodes and Differentiates into CD56brightNatural Killer Cells", Immunity, vol. 22, No. 3, (Mar. 1, 2005), 295-304.
Grzywacz, B., et al., "Natural Killer-Cell Differentiation by Myeloid Progenitors", Blood, vol. 117, No. 13, (Mar. 31, 2011), 3548-3558.
Kim, Soochan, et al., "Heterogeneity of Il-22 Producing Lymphoid . . . ", Immune Network, vol. 10, No. 4, [Online]. Retrieved from the Internet:<:ncbi.nlm.nih.gov/pmc/articles/PMC2939355/pdf/in-10-115.pdf>, (Aug. 4, 2010), 115-119.
Tang, Q., et al., "Development of IL-22-Producing NK Lineage Cells From Umbilical Cord Blood Hematopoietic Stem Cells in the Absence of Secondary Lymphoid Tissue", Blood, vol. 117, No. 15, (Apr. 14, 2011), 4052-4055.
Verneris, Michael R, et al., "The Phenotypic and Functional Characteristics of Umbilical Cord Blood and Peripheral Blood Natural Killer Cells", British Journal of Haematology, Wiley-Blackwell Publishing LTD, GB, vol. 147, No. 2, (Jan. 20, 2009), 185-191.
Adolfsson, Jorgen, et al., "Identification of Adult Flt3+ Lympho-Myeloid Stem Cells Lacking Erythro-Megakaryocytic Potential: A Revised Road Map for Blood Lineage Commitment", Supplemental Data, Cell, vol. 121, (2005), 3 pgs.

(Continued)

*Primary Examiner* — Gerald R Ewoldt
*Assistant Examiner* — Marianne Dibrino
(74) *Attorney, Agent, or Firm* — Schwegman Lundberg & Woessner, P.A.

(57) ABSTRACT

The present invention relates generally to methods to prepare NK and LTi-like, NK22 cells from HSCs and uses of those cells.

6 Claims, 24 Drawing Sheets

(56) References Cited

OTHER PUBLICATIONS

Adolfsson, Jorgen, et al., "Identification of Flt3+ Lympho-Myeloid Stem Cells Lacking Erythro-Megakaryocytic Potential: A Revised Road Map for Adult Blood Lineage Commitment", *Cell*, vol. 121, (2005), 295-306.

Bell, J. Jeremiah, et al., "The earliest thymic progenitors for T cells possess myeloid lineage potential", *Nature*, 452(7188), (2008), 764-767.

Bell, J. Jeremiah, et al., "The earliest thymic progenitors for T cells possess myeloid lineage potential", Supplementary Information, *Nature*, 452(7188), (2008), 1-6.

Bennett, Ian M., et al., "Definition of a Natural Killer NKR-PIA+/CD56−/CD16− Functionally Immature Human NK Cell Subset That Differentiates In Vitro in the Presence of Interleukin 12", *J. Exp. Med.*, 184(5), (1996), 1845-1856.

Blasius, Amanda L., et al., "Development and function of murine B220+ CD11c+ NK1.1+ cells identify them as a subset of NK cells", *J. Exp. Med.*, 204(11), (2007), 2561-2568.

Bonnefoix, Thierry, et al., "Fitting limiting dilution experiments with generalized linear models results in a test of the single-hit Poisson assumption", *Journal of Immunological Methods*, 194(2), (1996), 113-119.

Briard, Diane Briard, et al., "Fibroblasts from Human Spleen Regulate NK Cell Differentiation from Blood CD34+ Progenitors Via Cell Surface IL-15$^1$", *The Journal of Immunology*, 168, (2002), 4326-4332.

Buckley, Rebecca H., et al., "Human severe combined immunodeficiency: Genetic, phenotypic, and functional diversity in one hundred eight infants", *The Journal of Pediatrics*, 130(3), (Mar. 1997), 378-387.

Chan, Carnie W., et al., "Interferon-producing killer dendritic cells provide a link between innate and adaptive immunity", *Nature Medicine*, 12(2), (2006), 207-213.

Cichocki, Frank, et al., "The transcription factor c-Myc enhances KIR gene transcription through direct binding to an upstream distal promoter element", *Blood*, 113(14), (2009), 3245-3253.

Colucci, Francesco, et al., "What Does It Take to Make a Natural Killer?", *Nature Reviews Immunology*, 3(5), (2003), 413-425.

Cooper, Megan A., "The biology of human natural killer-cell subsets", *TRENDS in Immunology*, 22(11), (Nov. 2001), 633-640.

Cupedo, Tom, et al., "Human fetal lymphoid tissue-inducer cells are interleukin 17-producing precursors to RORC+ CD127+ natural killer-like cells", *Nature Immunology*, 10(1), (2009), 66-74.

Fehniger, Todd A., et al., "Differential Cytokine and Chemokine Gene Expression by Human NK Cells Following Activation with IL-18 or IL-15 in Combination with IL-12: Implications for the Innate Immune Response", *The Journal of Immunology*, 162, (1999), 4511-4520.

Fogg, Darin K., et al., "A Clonogenic Bone Marrow Progenitor Specific for Macrophages and Dendritic Cells", *Science*, 311(5757), (2006), 83-87.

Freud, Aharon G., "Evidence for discrete stages of human natural killer cell differentiation in vivo", *J. Exp. Med.*, 203(4), (2006), 1033-1043.

Freud, Aharon G., et al., "Human natural killer cell development", *Immunological Reviews*, 214(1), (2006), 56-72.

Graf, Thomas, "Differentiation plasticity of hematopoietic cells", *Blood*, 99(9), (2002), 3089-3101.

Hanna, Jacob, et al., "Novel APC-like properties of human NK cells directly regulate T cell activation", *The Journal of Clinical Investigation*, 114(11), (Dec. 2004), 1612-1623.

Horny, H.-P., et al., "Lymph node morphology after allogeneic bone marrow transplantation for chronic myeloid leukemia: a histological and immunohistological study focusing on the phenotype of the recovering lymphoid cells", *Blut*, 57(1), (1988), 31-40.

Hughes, Tiffany, et al., "Interleukin-1β Selectively Expands and Sustains Interleukin-22+ Immature Human Natural Killer Cells in Secondary Lymphoid Tissue", *Immunity*, 32(6), (2010), 803-814.

Hughes, Tiffany, et al., "Interleukin-1β Selectively Expands and Sustains Interleukin-22+ Immature Human Natural Killer Cells in Secondary Lymphoid Tissue", Supplemental Information, *Immunity*, 32(6), (2010), 7 pgs.

Hughes, Tiffany, et al., "Stage 3 immature human natural killer cells found in secondary lymphoid tissue constitutively and selectively express the $T_H17$ cytokine interleukin-22", *Blood*, 113(17), (2009), 4008-4010.

Katsura, Yoshimoto, "Redefinition of lymphoid progenitors", *Nature Reviews Immunology*, 2(2), (2002), 127-132.

Kelly, Ryan M., et al., "Short-term inhibition of p53 combined with keratinocyte growth factor improves thymic epithelial cell recovery and enhances T-cell reconstitution after murine bone marrow transplantation", *Blood*, 115(5), (2010), 1088-1097.

Kondo, Motonari, et al., "Identification of Clonogenic Common Lymphoid Progenitors in Mouse Bone Marrow", *Cell*, 91, (1997), 661-672.

Li, Hao, et al., "Macrophage precursor cells produce perform and perform Yac-1 lytic activity in response to stimulation with interleukin-.2", *Journal of Leukocyte Biology*, vol. 56, (1994), 117-123.

Lotzova, Eva, et al., "Human natural killer cell development from bone marrow progenitors: analysis of phenotype, cytotoxicity and growth", *Nat. Immunity*, 12(4-5), (1993), 209-217.

Maher, Diane M., et al., "Ex Vivo Modeling of Oral HIV Transmission in Human Palatine Tonsil", *Journal of Histochemistry & Cytochemistry*, 53(5), (May 2005), 631-642.

Manz, Markus G., et al., "Prospective isolation of human clonogenic common myeloid progenitors", *Proc. Natl. Acad. Sci. USA*, 99(18), (2002), 11872-11877.

Marquez, Carlos, et al., "Identification of a Common Developmental Pathway for Thymic Natural Killer Cells and Dendritic Cells", *Blood*, 91(8), (1998), 2760-2771.

Martin, Matthew A., et al., "Analysis of the Human Fetal Liver Hematopoietic Microenvironment", *Stem Cells Dev.*, 14(5), (2005), 493-504.

Metcalf, Donald, "On Hematopoietic Stem Cell Fate", *Immunity*, 26, (2007), 669-673.

Miller, Jeffrey S., et al., "Differentiation of Natural Killer (NK) Cells From Human Primitive Marrow Progenitors in a Stroma-Based Long-term Culture System: Identification of a CD34+7+ NK Progenitor", *Blood*, 83(9), (1994), 2594-2601.

Miller, Jeffrey S., et al., "Human natural killer cells with polyclonal lectin and immunoglobulinlike receptors develop from single hematopoietic stem cells with preferential expression of NKG2A and KIR2DL2/L3/S2", *Blood*, 98(3), (2001), 705-713.

Miller, Jeffrey S., et al., "Single Adult Human CD34+/Lin−/CD38− Progenitors Give Rise to Natural Killer Cells, B-Lineage Cells, Dendritic Cells, and Myeloid Cells", *Blood*, 93(1), (1999), 96-106.

Mrózek, Ewa, et al., "Role of Interleukin-I5 in the Development of Human CD56+ Natural Killer Cells From CD34+ Hematopoietic Progenitor Cells", *Blood*, 87(7), (1996), 2632-2640.

Olweus, Johanna, et al., "CD64/FcγRI is a granulo-monocytic lineage marker on CD34+ hematopoietic progenitor cells", *Blood*, 85(9), (1995), 2402-2413.

Olweus, Johanna, et al., "Granulocytic and Monocytic Differentiation of CD34$^{hi}$ Cells Is Associated With Distinct Changes in the Expression of the PU.I-Regulated Molecules, CD64 and Macrophage Colony-Stimulating Factor Receptor", *Blood*, 88(10), (1996), 3741-3754.

Orkin, Stuart H., et al., "Hematopoiesis: An Evolving Paradigm for Stem Cell Biology", *Cell*, 132, (2008), 631-644.

Ortaldo, John R., et al., "Heterogeneity of Natural Killer Cells", *Annual Review of Immunology*, vol. 2, (Apr. 1984), 359-394.

Perez, Sonia A., et al., "A novel myeloid-like NK cell progenitor in human umbilical cord blood", *Blood*, 101(9), (2003), 3444-3450.

Perez, Sonia A., et al., "A potential role for hydrocortisone in the positive regulation of IL-15-activated NK-cell proliferation and survival", *Blood*, 106(1), (2005), 158-166.

Purton, Louise E., et al., "Limiting Factors in Murine Hematopoietic Stem Cell Assays", *Cell Stem Cell*, 1(3), (2007), 263-270.

Reddy, Pavan, et al., "Immunobiology of acute graft-versus-host disease", *Blood Reviews*, 17(4), (2003), 187-194.

(56) References Cited

OTHER PUBLICATIONS

Rosenzwajg, Michelle, et al., "CD13/N-aminopeptidase is involved in the development of dendritic cells and macrophages from cord blood CD34+ cells", *Blood*, 95(2), (2000), 453-460.

Rosmaraki, Eleftheria E., et al., "Identification of committed NK cell progenitors in adult murine bone marrow", *European Journal of Immunology*, 31, (Jun. 2001), 1900-1909.

Rothenberg, Ellen V., et al., "Negotiation of the T Lineage Fate Decision by Transcription-Factor Interplay and Microenvironmental Signals", *Immunity*, 26, (Jun. 2007), 690-702.

Roussel, Martine F., et al., "Myc rescue of a mutant CSF-I receptor impaired in mitogenic signalling", *Nature*, 353(6342), (1991), 361-363.

Sanchez, Maria Jose, et al., "Identification of a Common T/Natural Killer Cell Progenitor in Human Fetal Thymus", *J. Exp. Med.*, 180, (Aug. 1994), 569-576.

Sherr, Charles J., "Colony-Stimulating Factor-1 Receptor", *Blood*, 75(1), (1990), 1-12.

Sivori, Simona, et al., "Early expression of triggering receptors and regulatory role of 2B4 in human natural killer cell precursors undergoing in vitro differentiation", *Proc. Natl. Acad. Sci. USA*, 99(7), (2002), 4526-4531.

Spits, Hergen, et al., "Natural Killer or Dendritic: What's in a Name?", *Immunity*, 26(1), (Jan. 2007), 11-16.

Stary, Georg, et al., "Tumoricidal activity of TLR7/8-activated inflammatory dendritic cells", *J. Exp. Med.*, 204(6), (2007), 1441-1451.

Taieb, Julien, et al., "A novel dendritic cell subset involved in tumor immunosurveillance", *Nature Medicine*, 12(2), (Feb. 2006), 214-219.

Terstappen, Leon W.M.M., et al., "Sequential generations of hematopoietic cononies derived from single nonlineage-committed $CD34^+CD38^-$ progenitor cells", *Blood*, 77(6), (1991), 1218-1227.

Trifari, Sara, et al., "IL-22-producing $CD4^+$ T cells: Middle-men between the immune system and its environment", *Eur. J. Immunol.*, 40(9), (2010), 2369-2371.

Vosshenrich, Christian A. J., "A thymic pathway of mouse natural killer cell development characterized by expression of GATA-3 and CD127", *Nature Immunology*, 7(11), (Nov. 2006), 1217-1224.

Vosshenrich, Christian A. J., et al., "$CD11c^{lo}B220^+$ interferon-producing killer dendritic cells are activated natural killer cells", *J. Exp. Med.*, 204(11), (2007), 2569-2578.

Wada, Haruka, et al., "Adult T-cell progenitors retain myeloid potential", *Nature*, 452(7188), (2008), 768-772.

Wada, Haruka, et al., "Adult T-cell progenitors retain myeloid potential", Supplementary Information, *Nature*, 452(7188), (2008), 10 pgs.

Weissman, Irving L., et al., "Stem and Progenitor Cells: Origins, Phenotypes, Lineage Commitments,", *Annu. Rev. Cell Dev. Biol.*, 17, (2001), 387-403.

Wu, Li, et al., "Development of Dendritic-Cell Lineages", *Immunity*, 26, (Jun. 2007), 741-750.

Yu, Haixin, et al., "Flt3 Ligand Promotes the Generation of a Distinct $CD34^+$ Human Natural Killer Cell Progenitor That Responds to Interleukin-15", *Blood*, 92(10), (1998), 3647-3657.

\* cited by examiner

FIG. 10A

| Experiment | 1 Cell/Well | | | 10 Cells/Well | | | 1Cell/Well in Methylcellulose | | |
|---|---|---|---|---|---|---|---|---|---|
| | Cytokines Only | Stroma + Cytokines | HC + Stroma + Cytokines | Cytokines Only | Stroma + Cytokines | HC + Stroma + Cytokines | Cytokines Only | Stroma + Cytokines | HC + Stroma + Cytokines | Cloning Efficiency |
| BG118 CMP | 0 | 1.67 | 3.33 | 0 | 30 | 51.67 | 15 | 40 | 8.3 | 63.3 |
| BG119 CMP | 3.33 | 35 | 27.5 | 8.33 | 100 | 100 | 35 | 46.7 | 10 | 91.7 |
| BG120 CMP | 0 | | 17.5 | | 86.67 | 100 | 30 | 43.3 | 11.7 | 85 |
| BG121 CMP | 0 | 3.33 | 8.33 | 1.67 | 68.33 | 55 | 26.7 | 23.3 | 11.7 | 61.7 |
| BG122 CMP | 0 | 23.33 | 34.17 | 5 | 98.15 | 100 | 18.3 | 56.7 | 6.7 | 81.7 |
| Median | 0 | 13.3 | 17.5 | 3.3 | 86.7 | 100 | 26.7 | 43.3 | 10 | 81.7 |
| Average | 0.7 | 15.8 | 18.2 | 3.7 | 76.6 | 81.3 | 25 | 42 | 9.7 | 76.7 |

FIG. 10B

| Experiment | 1 Cell/Well | | | 10 Cells/Well | | | 1Cell/Well in Methylcellulose | | | |
|---|---|---|---|---|---|---|---|---|---|---|
| | Cytokines Only | Stroma + Cytokines | HC + Stroma + Cytokines | Cytokines Only | Stroma + Cytokines | HC + Stroma + Cytokines | Erythroid Colonies | Myeloid Colonies | Mixed Colonies | Cloning Efficiency |
| BG118 GMP | 0 | 8.33 | 15 | 0 | 50 | 36.7 | 0 | 55 | 0 | 55 |
| BG119 GMP | 1.7 | 21.7 | 25 | 5 | 100 | 100 | 0 | 83.3 | 0 | 83.3 |
| BG120 GMP | 0 | 31.7 | 29.2 | n.d. | 75 | 88 (5 per well) | 0 | 61.7 | 0 | 61.7 |
| BG121 GMP | 0 | 25 | 5 | 5 | 73.3 | 30 | 0 | 43.3 | 0 | 43.3 |
| BG122 GMP | 1.7 | 15 | 22.3 | 16.7 | 88.1 | 95 | 0 | 70 | 0 | 70 |
| Median | 0 | 21.7 | 22.3 | 5 | 75 | 88 | 0 | 61.7 | 0 | 61.7 |
| Average | 0.7 | 20.3 | 19.3 | 6.7 | 77.3 | 69.9 | 0 | 62.7 | 0 | 62.7 |

//
GENERATION OF NATURAL KILLER CELLS AND LYMPHOID TISSUE INDUCER-LIKE (LTI-LIKE) NK-22 CELLS

REFERENCE TO RELATED APPLICAITONS

This application is a U.S. National Stage Filing under 35 U.S.C. §371 from International Application No. PCT/US2011/063098, filed on Dec. 2, 2011, and published as WO 2012/075412 on 07 Jun. 2012 which claims priority under 35 U.S.C. 119(e) from U.S. Provisional Application Ser. No. 61/419,689 filed Dec. 3, 2010, which applications are herein incorporated by reference.

BACKGROUND OF THE INVENTION

Hematopoietic stem cells (HSCs) give rise to all blood lineages[1]. As HSCs differentiate along one lineage, they gradually lose the ability to develop into other lineages[2]. Hematopoietic differentiation involves lineage commitment, defined here as the initiation of developmental program(s) that lead to a particular cell fate. The accompanying inability to differentiate into other lineages has been referred to as lineage maintenance[3]. Lineage commitment and lineage maintenance are complementary processes that guide cell fate decisions. Thus, cells committed to a particular lineage have alternative developmental choices until lineage maintenance is complete[4].

Hematopoietic differentiation has been schematically depicted as a "tree of hematopoiesis", outlining the possible developmental choices. According to this prevailing schema, the decision between lymphoid and myeloid lineages occurs very early. However, alternative views have been proposed, including the existence of a common myelolymphoid progenitor[5-6]. Elucidation of hematopoietic developmental pathways and extrinsic stimuli that influence them is instrumental to understanding both normal and malignant hematopoiesis. In particular, factors that favor natural killer (NK) cell development could be used to exploit their activity against malignancies.

NK cells are innate immune effector cells. Their derivation from either lymphoid or myeloid lineages was debated early in their discovery. Further research showed that NK cells can be derived from common lymphoid progenitors (CLPs) and hence have been considered separate from myeloid lineage[8-9].

Human secondary lymphoid tissues (SLTs) contain IL-22 producing cells with an immature NK phenotype. The study of human IL-22 producing NK lineage cells is limited by their location in SLT. Accordingly, investigators use small quantities of material obtained from either aborted fetal tissue or surgical specimens, potentially in the setting of pathology.

SUMMARY OF THE INVENTION

Described herein is a novel method to generate NK cells, as well as LTi-like NK22 cells from HSCs. One embodiment provides a method to produce Lymphoid Tissue Inducer-Like (LTi-like) NK-22 cells comprising culturing CD34$^+$ cells (e.g., hematopoietic stem cells (HSCs) isolated from, for example, umbilical cord blood, peripheral blood and/or bone marrow) in the presence of at least one cytokine comprising IL-3, stem cell factor, FLT-3L, IL-7, IL-15 or a combination thereof, so as to produce LTi-like NK22 cells. In one embodiment, the CD34$^+$ cells initially cultured in the presence of IL-3 are further cultured in the absence of IL-3.

In another embodiment, the CD34$^+$ cells are not cultured in the presence of IL-15. In one embodiment, the cells are cultured for about 7 to about 28 days, including about 21 days. In another embodiment, the cells are cultured for longer, including for about 29 to about 45, about 50, about 55, about 60 etc days, such as about 35 days.

One embodiment provides for culturing the CD34$^+$ cells in the presence of stroma (e.g., obtained from bone marrow, cell lines or fibroblasts). In one embodiment, the CD34$^+$ cells are seeded onto a stromal cell line. In another embodiment, the stromal cells are irradiated prior to the CD34$^+$ cells being seeded thereon.

In one embodiment, the CD34$^+$ cells are cultured in the presence of hydrocortisone (HDC). In another embodiment, after culturing the CD34$^+$ cells in presence of at least one cytokine comprising IL-3, stem cell factor, FLT-3L, IL-7, IL-15 or a combination thereof, the cells are then cultured in the presence of IL-1β and/or IL-23.

In one embodiment, the LTi-like NK22 cells express IL-22. In one embodiment, the LTi-like NK22 cells are CD56$^{+/-}$CD 117$^{high}$CD94$^-$. In one embodiment, the LTi-like NK22 cells express at least one of NKp44, CD-161, CCR6, aryl hydrocarbon receptor (AHR), ROR-γτ, NKp46, IL-1 receptor (CD-121) or a combination thereof. In one embodiment, the LTi-like NK22 cells do not express granzyme, perforin, CD-7 and/or LFA-1.

One embodiment provides a method to produce a transgenic NK or LTi-like NK22 cell comprising tranfecting CD34$^+$ HSC with a specified gene, differentiating the transfected cell into a NK or LTi-like NK22 cell so as to produce a transgenic NK or LTi-like NK22 cell.

Another embodiment provides a method to facilitate immune recovery after chemotherapy or bone marrow transplantation comprising administering an effective amount of the cells produced the methods described herein to a subject in need thereof so as to facilitate immune recovery after chemotherapy or bone marrow transplantation.

One embodiment provides for a method to treat cancer and/or viral infection comprising administering an effective amount of the cells produced by the methods described herein to a subject in need thereof so as to treat cancer and/or viral infection.

One embodiment provides for a method to treat Crohn's disease, ulcerative colitis, and/or inflamatory bowel disease comprising administering an effective amount of the cells produced by the methods described herein to a subject in need thereof so as to treat Crohn's disease, ulcerative colitis, and/or inflamatory bowel disease.

BRIEF DESCRIPTION OF THE FIGURES

FIGS. 10A-B: CMPs and GMPs can give rise to NK cells under the influence of stroma and hydrocortisone. CMP (upper section) and GMP (lower section) were double sorted from UCB and deposited in 96 well plates at 1 cell/well or 10 cells/well (see methods for details). Culture conditions included cytokine alone (IL-3, IL-7, IL-15, SCF and FLT3L), +/−stroma, +/−stroma and HDC or methylcellulose. 60 replicates were performed for each donor (n=5). At the end of the culture period each well was assayed for NK cells using FACS. Shown are the percentage of wells that contained NK cells. Cells cultured in methylcellulose were examined for erythroid, myeloid and mixed colonies. The bottom two rows show the median and average for the all experiments (n=300 wells using 5 separate donors for each condition).

DETAILED DESCRIPTION OF THE INVENTION

Figure 1A:
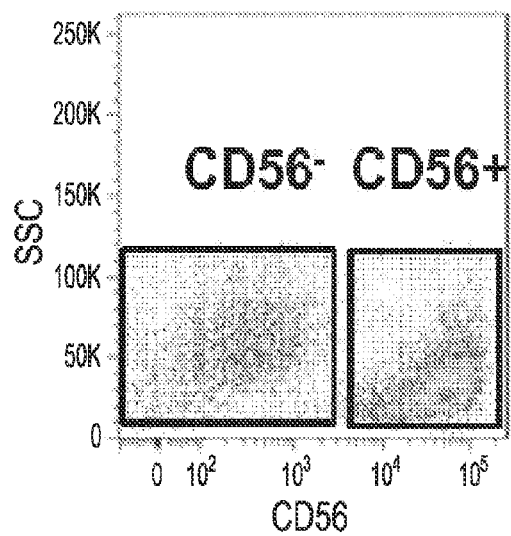
FIGS. 1A-F: HSC-derived CD56$^{+/-}$CD117$^{high}$CD94$^-$ NK cells produce IL-22 upon stimulation. A) Cultures at D+21 show heterogenous CD56 expression. B and C) Purified CD56+ and CD56– cells assessed for IL-22 mRNA expression and protein expression at rest and after activation with IL-1β (10 ng/ml) and IL-23 (40 ng/ml). D) FACS at day+28 of culture, showing that the CD56+ fraction can be divided into CD117$^{high}$CD94$^-$ and CD117$^{low/-}$CD94$^+$ fractions. E and F) CD117$^{high}$CD94$^-$ and CD117$^{low/-}$CD94$^+$ fractions were FACS purified and assessed for IL-22 mRNA expression and protein expression at rest and after activation with IL-1β (10 ng/ml) and IL-23 (40 ng/ml). Results are representative of >3 donors.

Described herein is a novel method to generate NK cells, as well as LTi-like NK22 cells from HSCs. At present, NK cells can be obtained from the peripheral blood of individuals. However, LTi-like NK-22 cells exist only in secondary lymphoid tissues (i.e., lymph nodes). Therefore, there is no way to obtain these cells from healthy donors without invasive procedures. Both of these cell types have in pre-clinical and clinical applications (e.g., therapy).

As used herein, the terms below are defined by the following meanings:

Natural killer cells (or NK cells) are a type of cytotoxic lymphocyte that constitute a component of the innate immune system. NK cells play a role in the rejection of tumors and cells infected by viruses. They kill cells by releasing small cytoplasmic granules of proteins called perforin and granzyme or through the expression of death receptors (FasL and TRAIL) that cause the target cell to die.

NK cells are defined as large granular lymphocytes (LGL). They usually do not express T-cell antigen receptors (TCR) or Pan T marker CD3 or surface immunoglobulins (Ig) B cell receptors, but they usually express the surface markers CD16 (FcγRIII) and CD56 in humans, NK1.1 in C57BL/6 mice. Up to 80% of human NK cells also express CD8.

"LTi-like, NK22 cells": the terminology of these cells is rapidly changing, but the cell type has been referred to in the literature and herein using the following nomenclature: 1) lymphoid tissue inducer cells (LTi cells), 2) LTi-like cells, 3) Innate lymphoid cells (ILCs) and 4) NK22 cells.

"Progenitor cells" are cells produced during differentiation of a stem cell that have some, but not all, of the characteristics of their terminally-differentiated progeny. Defined progenitor cells are committed to a lineage, but not to a specific or terminally-differentiated cell type.

The terms "isolated" or an "enriched population" refers to a cell or cells which are not associated with one or more cells or one or more cellular components that are associated with the cell or cells in vivo.

A "subject" is a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, and orangutan) rat, sheep, goat, cow and bird.

An "effective amount" generally means an amount which provides the desired local or systemic effect and/or performance, particularly for treating a condition of interest. For example, an effective dose is an amount sufficient to affect a beneficial or desired clinical result. Said dose could be administered in one or more administrations and could include any preselected amount of cells. The precise determination of what would be considered an effective dose may be based on factors individual to each subject, including their size, age, size of the damage, and amount of time since the damage occurred or the disease began. One skilled in the art, specifically a physician, would be able to determine the number of cells that would constitute an effective dose.

"Expansion" refers to the propagation of cells without differentiation.

"Self-renewal" refers to the ability to produce replicate daughter cells having differentiation potential that is identical to those from which they arose. A similar term used in this context is "proliferation."

As used herein, "treat," "treating" or "treatment" includes treating, reversing, ameliorating, or inhibiting an injury or disease-related condition or a symptom of an injury or disease-related condition.

"Co-administer" can include simultaneous and/or sequential administration of two or more agents/cell types.

The terms "comprises," "comprising," and the like can have the meaning ascribed to them in U.S. Patent Law and can mean "includes," "including" and the like. As used herein, "including" or "includes" or the like means including, without limitation.

Isolation, Growth, Differentiation and Characterization of Cells

The present invention provides methods to generate NK cells, as well as LTi-like NK22, cells from HSCs. At present, the only way to obtain NK cells is through a blood draw or leukapheresis. These cells are resistant to gene manipulation. However, using this methodology, gene manipulation could be introduced into a HSC, and then the HSC could be used to generate NK cells. Currently, there is no method to obtain LTi-like NK-22 cells, other than lymph node biopsy, tonsilectomy or the study of human abortions. The isolation, growth and characterization of such cells are discussed in detail in the Examples below.

In addition to that provided in the Examples, during the methods described herein (isolation, proliferation, differentiation, manipulation (e.g., transfection etc.) the cells described herein can be cultured in culture medium that is well established in the art and commercially available from the American Type Culture Collection (ATCC). Such media include, but are not limited to, Dulbecco's Modified Eagle's Medium (DMEM), DMEM F12 medium, Eagle's Minimum Essential Medium, F-12K medium, Iscove's Modified Dulbecco's Medium, or RPMI-1640 medium. It is within the skill of one in the art to modify or modulate concentrations of media and/or media supplements as needed for the cells used. It will also be apparent that many media are available as low-glucose formulations, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements, and bovine embryonic fluid. It is understood that sera can be heat-inactivated at 55-65° C. if deemed necessary to inactivate components of the complement cascade. Modulation of serum concentrations, or withdrawal of serum from the culture medium can also be used to promote survival of one or more desired cell types. In one embodiment, the cells are cultured in the presence of FBS/or serum specific for the species cell type. For example, cells can be isolated and/or expanded with total serum (e.g., FBS) concentrations of about 0.5% to about 5% or greater including about 5% to about 15%. Concentrations of serum can be determined empirically.

Additional supplements can also be used to supply the cells with trace elements for optimal growth and expansion. Such supplements include insulin, transferrin, sodium selenium, and combinations thereof. These components can be included in a salt solution such as, but not limited to, Hanks' Balanced Salt Solution® (HBSS), Earle's Salt Solution®, antioxidant supplements, MCDB-201® supplements, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to, amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine. β-mercaptoethanol can also be supplemented in cell culture media.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Cells in culture can be maintained either in suspension or attached to a solid support, such as extracellular matrix components and synthetic or biopolymers. Cells often require additional factors that encourage their attachment to a solid support (e.g., attachment factors) such as type I, type II, and type IV collagen, concanavalin A, chondroitin sulfate, fibronectin, "superfibronectin" and/or fibronectin-like polymers, gelatin, laminin, poly-D and poly-L-lysine, Matrigel™, thrombospondin, and/or vitronectin.

The maintenance conditions of cells can also contain cellular factors that allow cells of the invention to remain in an undifferentiated form. It may be advantageous under conditions where the cell must remain in an undifferentiated state of self-renewal for the medium to contain epidermal growth factor (EGF), platelet derived growth factor (PDGF), leukemia inhibitory factor (LIF), basic fibroblast growth factor (bFGF) and combinations thereof. It is apparent to those skilled in the art that supplements that allow the cell to self-renew (e.g., to produce replicate daughter cells having differentiation potential that is identical to those from which they arose; a similar term used in this context is "proliferation"), but not differentiate should be removed from the culture medium prior to differentiation. It is also apparent that not all cells will require these factors. In fact, these factors may elicit unwanted effects, depending on the cell type.

The cells described herein can be selected based on the markers (gene and/or protein) described herein. Accordingly, positive selection methods can be used, either alone or together with the methods described above, to identify and/or isolate the cells of the invention. Methods of positive selection can include visual selection, using microscopy and/or other means of detection, including, but not limited to, immunoblotting, immunofluorescence, and/or enzyme-linked immunosorbent assay. Other methods of positive selection can also include, but are not limited to, additional selective culture techniques (e.g., variable cell densities or amounts of $CO_2$), flow cytometry, RT-PCR, and/or microchip-based methods of cell separation. Negative selection methods may also be used.

Inducing Cells to Differentiate

Using appropriate growth factors, chemokines and/or cytokines, as described herein, cells can be induced to differentiate to form different cell types.

For example, IL-3, IL-7, IL-15, IL-2 and other factors, such as stem cell factor and FLT-3L (that will be encompassed by the term cytokine herein) can differentiate HSC to LTi-like NK22 cells. Various stress molecules involved in the cellular response to stress, e.g., viral infection, can also be used to differentiate HSC to NK or LTi-like, NK22 cells. For example, IL-12, IL-15, IL-18, IL-2, IL-21, and/or CCL5.

Uses for NK and LTi-like, NK22 Cells

NK and LTi-like NK22 cells of the invention can be used in clinical, preclinical and research settings. NK cells play a role in the rejection of tumors/tumor cells and cells infected with viruses. Thus, NK and LTi-like, NK-22 (ILC) cells of the invention can be used in the treatment of cancer (including, but not limited to, carcinoma (e.g., breast, prostate, lung, pancreas, liver (e.g., hepatocarcinoma) or colon cancer), sarcoma (e.g., bone, cartilage, neuronal or fat (e.g., liposarcoma) cancers), lymphoma, leukemia (blood type cancers), blastomas (e.g., hepatoblastoma), as well as viral infections (e.g., DNA viruses (Adenoviruses, Herpesviruses (e.g., Herpes simplex, type 1, Herpes simplex, type 2, Varicella-zoster virus, Epstein-barr virus, Human cytomegalovirus, Human herpesvirus, type 8), Papillomaviridae (e.g., Human papillomavirus), Poxviruses (e.g., Smallpox), Parvoviruses (e.g., Human bocavirus, Parvovirus B19), Hepadnaviridae (e.g., Hepatitis B virus) and/or Reoviruses (e.g., Rotavirus)), RNA viruses (Picornaviruses (e.g., coxsackievirus, hepatitis A virus, poliovirus, rhinovirus), Togaviruses (Rubella virus), Orthomyxoviruses (e.g., Influenza virus), and/or Rhabdoviruses (e.g., Rabies virus)), or reverse transcribing viruses (including, but not limited to, Retroviruses and Hepadnaviruses, Retroviridae (human immunodeficiency virus (HIV)), Metaviridae, Pseudoviridae, Caulimoviridae, Hepadnaviridae)).

LTi-like, NK-22 cells may play a role in the homeostasis of secondary lymphoid tissue. Thus, LTi-like, NK-22 cells has applications in facilitating immune recovery after chemotherapy and bone marrow transplantation, as well as in the generation of 3-dimensional secondary lymphoid tissues ex vivo.

Additionally, LTi-like, NK-22 or ILC cells find use in bone marrow transplantation (by facilitating mucosal tissue injury repair vis-à-vis IL22). ILC cells can also facilitate immune reconstitution by repairing stromal injury to secondary lymphoid tissues and accelerating adaptive immune responses. Also, the high expression of OX40 ligand and BAFF on these cells can facilitate memory responses. ILC cells can also treat Crohn's Disease/Ulcerative colitis (Inflamatory Bowel Disease) (by facilitating intestinal mucosal repair as well as the generation of intestinal secondary mucosal tissue including Peyer's patches, cytopatches and intestinal lymphoid follicles).

Cells described herein can benefit from co-culturing with another cell type. Such co-culturing methods arise from the observation that certain cells can supply yet-unidentified cellular factors that allow the cell to differentiate into a specific lineage or cell type. These cellular factors can also induce expression of cell-surface receptors, some of which can be readily identified by monoclonal antibodies. Generally, cells for co-culturing can be selected based on the type of lineage one skilled in the art wishes to induce, and it is within the abilities of the skilled artisan to select the appropriate cells for co-culture.

Methods of identifying and subsequently isolating differentiated cells from their undifferentiated counterparts can be carried out by methods well known in the art. Cells that have been induced to differentiate can be identified by selectively culturing cells under conditions whereby differentiated cells outnumber undifferentiated cells. These conditions include, for example, extending the amount of time that cells are grown in culture, such that survival of a desired cell type is encouraged. Many primary cells achieve senescence, and fail to divide, or die, after a period of time. Other conditions comprise modulating the type and concentration of serum, or culturing the cells in the presence or absence of growth factors and/or cytokines that induce differentiation to another cell type. Differentiation can also be advantageously achieved by modulation of serum concentrations, or withdrawal of serum from the culture. Other methods of inducing differentiation can include, but are not limited to, modulating the acidity of the culture medium, as well as the oxygen and carbon dioxide levels during culture.

Similarly, differentiated cells can be identified by morphological changes and characteristics that are not present on their undifferentiated counterparts, such as cell size, the number of cellular processes, and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and/or enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads (selection or depletion techniques (Miltenyi)), or combinations thereof. One embodiment of the invention envisions the use of FACS to identify and separate cells based on cell-surface antigen expression. It is understood that the methods of identification and separation are not limited to analysis of differentiated cell types, but can also be used to identify undifferentiated cell types.

Cells described herein could also be used in cell replacement therapies. The cells can be administered to a tissue of interest in a subject to supplement functioning cells or replace cells, which have lost function (e.g., reduced function as compared to a control cell). Alternatively, methods of providing differentiated cells are also contemplated.

NK and LTi-like NK22 cells of the invention can be used for many diverse clinical and pre-clinical applications, which can include, but are not limited to, use in toxicological or genomic screening methods, determination of levels of enzymes, as well as treatment of diseases. NK and LTi-like NK22 cells of the invention can provide useful cultured cell types for high-throughput toxicological or genomic screening. The cells can be cultured in, for example, 96-well or other multi-well culture plates to provide a system for high-throughput screening of, for example, target cytokines, chemokines, growth factors, or pharmaceutical compositions in pharmacogenomics or pharmacogenetics.

Thus, the present invention provides for use of NK and LTi-like NK22 cells to detect cellular responses (e.g., toxicity) to bioactive (biologic or pharmacologic) agents, comprising contacting a culture of cells, or the differentiated progeny thereof, with one or more biologic or pharmacologic agents, identifying one or more cellular response to the one or more biologic or pharmacologic agents, and comparing the cellular responses of the cell cultures to the cellular responses of control cultures.

Administration of Cells

For the purposes described herein, either autologous, allogeneic or xenogeneic cells of the invention can be administered to a subject, either in differentiated or undifferentiated form, genetically altered or unaltered, by direct injection to a tissue site, systemically, on or around the surface of an acceptable matrix, encapsulated or in combination with a pharmaceutically acceptable carrier.

Cells of the invention can be administered to a subject by a variety of methods known in the art. For example, cells can be administered to a subject by localized or systemic injection.

In one embodiment, a cell suspension is drawn up into a syringe and administered to a subject. Multiple injections may be made using this procedure. The use of such cellular suspension procedures provides many advantages. For example, these methods direct cells to any predetermined site and are relatively non-traumatic.

Typically, the number of cells transplanted into a subject will be a "therapeutically effective amount." As used herein, a "therapeutically effective amount" refers to the number of transplanted cells that are required to effect treatment of the particular injury, or disease for which treatment is sought. For example, where the treatment is for tissue injury, transplantation of a therapeutically effective amount of cells will typically produce a reduction in the amount and/or severity of the symptoms associated with the injury. Persons of skill in the art will understand how to determine proper cell dosages.

As desired, cells of the invention and their differentiated progeny can be induced to proliferate and/or differentiate in vivo by administering to the host, any growth factor(s), cytokine(s) or pharmaceutical composition(s) that will induce proliferation and differentiation of the cells. These growth factor(s), cytokine(s) or pharmaceutical composition(s) include any growth factor, cytokine or pharmaceutical composition known in the art, including the growth factors and cytokines described herein for in vitro proliferation and differentiation.

Exogenous factors (e.g., cytokines, differentiation factors and other factors) can be administered prior to, after or concomitantly with the cells of the invention. For example, a form of concomitant administration would comprise combining a factor of interest in the culture media and/or pharmaceutically acceptable carrier prior to administration. Doses for administrations are variable, may include an initial administration followed by subsequent administrations; but nonetheless, can be ascertained by the skilled artisan, from this disclosure, the documents cited herein, and the knowledge in the art.

A parameter involved in the therapeutic use of NK and/or LTi-like NK22 cells of the invention is the quantity of cells necessary to achieve an optimal effect. Different scenarios may require optimization of the amount of cells injected into a tissue of interest. For example, the quantity of cells to be administered will vary for the subject being treated. In one embodiment, between $10^4$ to $10^8$, more preferably $10^5$ to $10^7$, and most preferably $3 \times 10^7$ cells and optionally, 50 to 500 µg/kg per day of a cytokine can be administered to a human subject. However, the precise determination of what would be considered an effective dose may be based on factors individual to each patient, including their size, age, size tissue damage, and amount of time since the damage occurred. Therefore, dosages can be readily ascertained by those skilled in the art from this disclosure and the knowledge in the art.

Another parameter involved in the use of cells of the invention is the purity of the population. Those skilled in the art can readily determine the percentage of specific cell types/phenoptypes of the invention in a population using various well-known methods, such as fluorescence activated cell sorting (FACS). Preferable ranges of purity in populations comprising cells described herein are about 1 to about 5%, about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90% to about 95% or about 95 to about 100%. Purity of the cells can be determined according to the cell surface marker profile within a population. Dosages can be readily adjusted by those skilled in the art (e.g., a decrease in purity may require an increase in dosage).

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired. Examples of compositions comprising cells of the invention include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, which is incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (e.g., purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes.

Viscosity of the compositions, if desired, can be maintained at the selected level using a pharmaceutically acceptable thickening agent. Methylcellulose is readily and economically available and is easy to work with. Other suitable thickening agents include, for example, xanthan gum, carboxymethyl cellulose, hydroxypropyl cellulose, carbomer, and the like. The concentration of the thickener will depend upon the agent selected. The point is to use an amount, which will achieve the selected viscosity. Viscous compositions are normally prepared from solutions by the addition of such thickening agents.

A pharmaceutically acceptable preservative or cell stabilizer can be employed to increase the life of the compositions. If preservatives are used, it is well within the purview of the skilled artisan to select compositions that will not affect the viability or efficacy of the cells as described herein.

Those skilled in the art will recognize that the components of the compositions should be selected to be chemically inert. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable and may include an initial administration followed by subsequent administrations; but nonetheless, can be ascertained by the skilled artisan, from this disclosure, the documents cited herein, and the knowledge in the art.

Genetically-Modified Cells of the Invention

Cells, such as the cells described herein, can be genetically altered/modified.

For example, HSC can be genetically modified prior to differentiation to NK or LTi-like, NK22 cells. Cells described herein can be genetically modified by introducing heterologous DNA or RNA into the cell by a variety of recombinant methods known to those of skill in the art. These methods are generally grouped into four major categories: (1) viral transfer, including the use of DNA or RNA viral vectors, such as retroviruses, including lentiviruses, Simian virus 40 (SV40), adenovirus, alpha virus, including Sindbis virus, and bovine papillomavirus, for example; (2) chemical transfer, including calcium phosphate transfection and DEAE dextran transfection methods; (3) membrane fusion transfer, using DNA-loaded membranous vesicles such as liposomes, red blood cell ghosts and protoplasts, for example; and (4) physical transfer techniques, such as microinjection, microprojectile, electroporation, nucleofection or direct "naked" DNA transfer.

Cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids or PNAs), or by ribozyme technology, for example. Insertion of one or more pre-selected DNA sequences can be accomplished by homologous recombination or by viral integration into the host cell genome. Methods of non-homologous recombination are also known, for example, as described in U.S. Pat. Nos. 6,623,958, 6,602,686, 6,541,221, 6,524,824, 6,524,818, 6,410,266, 6,361,972.

The desired gene sequence can also be incorporated into the cell, particularly into its nucleus, using a plasmid expression vector and a nuclear localization sequence. Methods for directing polynucleotides to the nucleus have been described in the art. For example, signal peptides can be attached to plasmid DNA to direct the DNA to the nucleus for more efficient expression.

The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) in specific cell compartments (including, but not limited to, the cell membrane).

Any of the transfection or transduction techniques can also be applied to introduce a transcriptional regulatory sequence into the cells of the invention or progeny to activate a desired endogenous gene. This can be done by both homologous (e.g., U.S. Pat. No. 5,641,670) or non-homologous (e.g., U.S. Pat. No. 6,602,686) recombination.

Successful transfection or transduction of target cells can be demonstrated using genetic markers. The green fluorescent protein of *Aequorea victoria*, for example, has been shown to be an effective marker for identifying and tracking genetically modified hematopoietic cells. Alternative selectable markers include the β-Gal gene, the truncated nerve growth factor receptor, and drug selectable markers (including but not limited to NEO, MTX, hygromycin).

EXAMPLES

The following examples are provided in order to demonstrate and further illustrate certain embodiments and aspects of the present invention and are not to be construed as limiting the scope thereof.

Example I

Human secondary lymphoid tissues (SLTs) contain IL-22 producing cells with an immature NK phenotype. The study of human IL-22 producing NK lineage cells is limited by their location in SLT. Accordingly, investigators use small quantities of material obtained from either aborted fetal tissue or surgical specimens, potentially in the setting of pathology. To date, no reports have investigated the development of these cells from hematopoietic stem cells (HSCs).

Described herein is the generation of large numbers of these cells from hematopoietic stem cells (HSCs) (>1000× expansion). HSC-derived NK22 cells show a $CD56^{+/-}CD117^{high}CD94^-$ phenotype, consistent with stage III NK progenitors. Like freshly isolated SLT stage III cells, stem cell derived NK22 cells express NKp44, CD161, CCR6, IL1 receptor, aryl hydrocarbon receptor and ROR-γτ. IL-1β and IL-23 stimulation results in significant IL-22 production and supernatant from these cells results in increase in CD54 expression on mesenchymal stem cells. Thus, IL-22 producing NK cells can be generated in the absence of SLT. These HSC-derived NK22 cells are valuable source for clinical and nonclinical settings.

Recent studies have identified human NK lineage cells including: lymphoid tissue inducer (LTi) cells[1,2], stage III NK progenitors[3] and/or NK22 cells[4] that reside in secondary lymphoid tissue (SLT) and produce IL-22. While these cells differ by tissue location (tonsil, lymph node and Peyer's patches) and age of donor (fetal and adult tissues), they have some unifying features including the expression of Th17/Th22-associated transcription factors (i.e., ROR-γτ and aryl hydrocarbon receptor (AHR)[2,4] and surface phenotype characteristic of developing NK cells (including CD 117, CD 127, NKp46, NKp44, CCR6 and the lack of granzyme, perforin and killer Ig receptors (KIR))[3-5]. IL-22 producing NK lineage cells are functionally characterized by low/ absent cytotoxicity and the induction of adhesion molecules on mesenchymal stem cells (MSCs)[3-5].

Materials and Methods

NK Differentiation Cultures: Briefly, the murine embryonic liver cell line EL08.ID2 was cultured on gelatinized plates at 32° C. in 40.5% α-MEM (Invitrogen, CA), 50% myelocult (M5300, Stem Cell Technologies, Vancouver, Canada), 7.5% FBS, with β-mercaptoethanol (50 µM/L), glutamax (2 mM), and penicillin (100 U/ml)-streptomycin (100 U/ml). $CD34^+$ cells were isolated from umbilical cord blood (UCB) using magnetic bead selection and cultured on irradiated EL08.1D2 (3000 rads) in the presence of IL-3 (first week), FLT3L and stem cell factor (SCF), IL-7 and IL-15 as previously described[6]

FACS: At specified times, cells were washed with PBS, stained with antibodies and subjected to FACS. Antibodies included: CD56, CD 117, CD94, CCR6, CD 161 (BD biosciences), IL-1βR(R&D systems), NKp30 NKp44, NKp46 (Beckman Coulter), AHR (Santa Cruz), ROR-c, CD 127, and IL-22 (eBiosceices). Intracellular staining was performed using cytofix/cytoperm (BD Biosciences). Data was analyzed using FlowJo software.

PCR: RNA was isolated from cells and reverse transcribed using standard techniques. PCR was performed using primers for IL-22 (Forward: CCCATCAGCTC-CCACTGC (SEQ ID NO:1), Reverse: GGCACCACCTC-CTGCATATA (SEQ ID NO:2)) and GAPDH (Forward: GTCGGAGTCAACGGATT (SEQ ID NO:3), Reverse: AAGCTTCCCGTTCTCAG (SEQ ID NO:4)).

IL-22 ELISA: IL-22 was detected by ELISA using duoset (R&D, Minneapolis, Minn.) according to manufacturer's specifications. In some experiments recombinant human IL-1β and/or IL-23 (R&D systems, Minneapolis, Minn.) was added in specified amounts.

Tonsil Cell Suspensions: Palatine tonsil samples were obtained from the Tissue Procurement Facility at the University of Minnesota. Patients or parent/legal guardians provided written consent to use clinical materials for research. All studies were IRB approved. Single cell suspensions were prepared from fresh tonsil as described previously[12].

MSC co-cultures: Supernatant from specified NK populations was co-cultured with MSCs for 48 hrs and MSCs were subjected to FACS for ICAM (CD54) (BD Biosciences) expression.

Results and Discussion

Figure 1B:
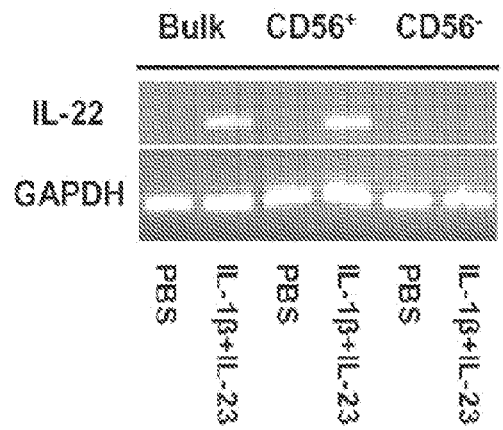
Figure 1C:
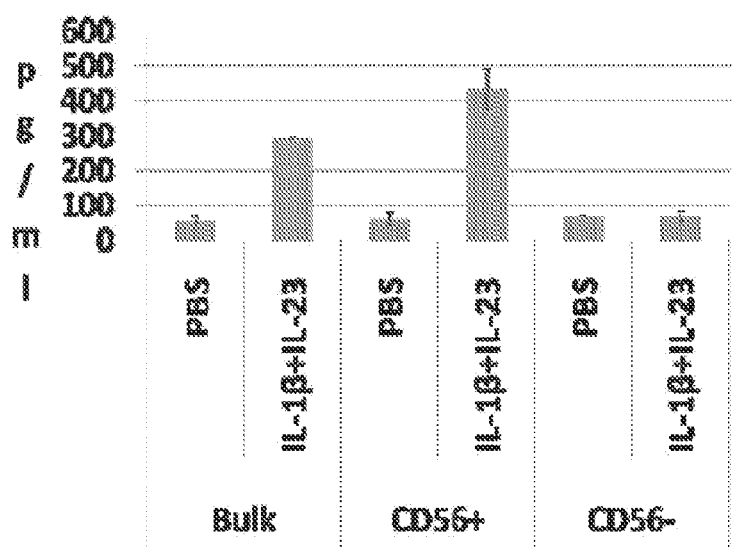
Figure 1D:
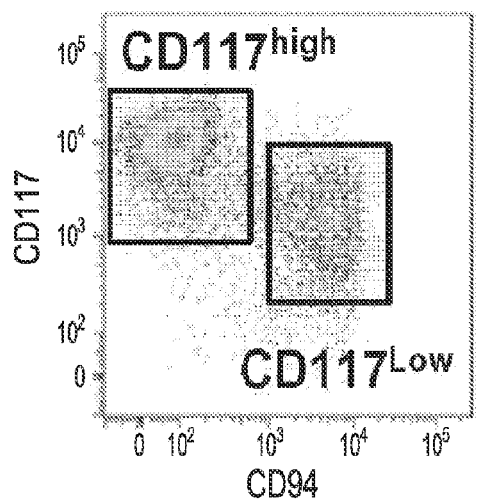
Figure 1E:
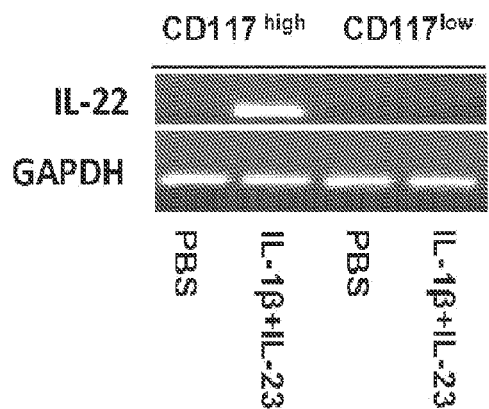
Figure 1F:
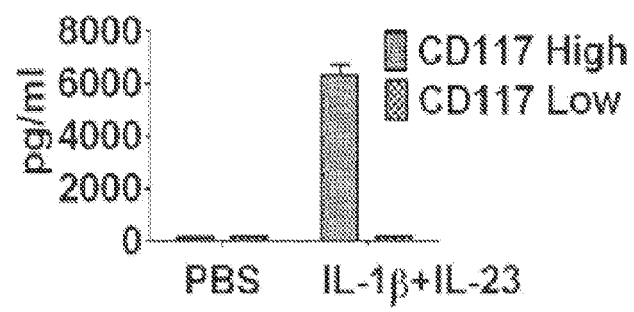

Recently, LTi cells have been isolated from human fetal tissues[1,2]. These cells lack CD56, produce IL-22 and acquire CD56 upon culture with IL-15[2]. Alternatively, $CD56^{+/-}$ Kp44$^+$ cells that produce IL-22 have been isolated from human gastrointestinal lymphoid tissue[4]. Still others have identified IL-22 producing stage III NK progenitors that are $CD56^{+/-}CD117^+CD94^-$[3]. It is herein described whether IL-22 producing NK cells can be derived from $CD34^+$ UCB HSCs. As shown in FIG. 1A, after 21 days of culture, a mixture $CD56^-$ and $CD56^+$ cells are present. The majority of $CD56^-$ cells are lin– and most express CD7 (not shown). Based on CD56 expression, two populations were purified and assayed for IL-22 transcripts. Neither constitutively produced IL-22. However, following IL-1β/IL-23 stimulation, only $CD56^+$ cells produced IL-22 mRNA (FIG. 1b) and protein (FIG. 1c). Prior studies show that stage III NK cells (lin$^-$CD56$^{+/-}$CD117$^{high}$CD94$^-$) isolated from tonsils produce IL-22, while the more mature stage 1V cells ($CD56^{+/-}$ CD117$^{low}$/CD94$^+$) do not[3]. Using this in vitro NK cell developmental system we characterized similar populations (FIG. 1d and [6]). To test for IL-22 production, these cells were FACS purified. After stimulation, IL-22 mRNA and protein were only detected in the stage 1 μl, $CD56^{+/-}CD117^{high}CD94^-$ cells (FIGS. 1E and 1F).

Figure 2A:
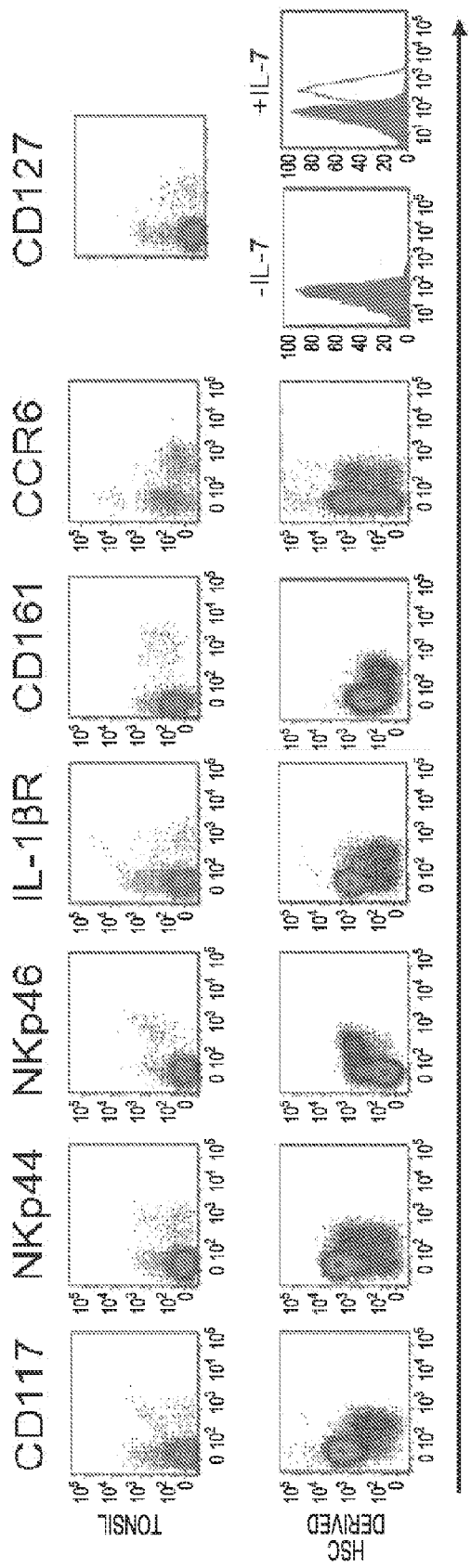
FIGS. 2A-D: HSC-derived CD56$^{+/-}$CD117$^{high}$CD94$^-$ NK cells are phenotypically and functionally similar to SLT-derived stage III cells or NK22 cells. HSC-derived CD56$^{+/-}$ $CD117^{high}CD94^-$ NK cells were compared to $CD45^+CD3^-$ $CD56^{+/-}CD117^+$ lymphoid fraction of tonsillar mononuclear cells for the expression of receptors, including: A) CD117, NKp44, NKp46, IL-1R, CD161, and CCR6. CD127 expression is shown with cultures containing IL-7 (right) and when IL-7 is removed from the media for 7 days (open histogram). FACS plots are gated on the $CD56^{+/-}CD117^{high}CD94^-$ cell fraction. B) AHR and RORc, and C) IL-22 (note in vitro derived cells were stimulated with IL-1β and IL-23 as in FIG. 1). D) Supernatant from HSC-derived NK cells can increase expression of ICAM-1 on MSCs. Shown are the FACS plots of ICAM-1 expression after 48 hours of co-culture with media supplemented with IL-1β and IL-23 (closed histogram) or with supernatant from in vitro derived $CD56^{+/-}CD117^{high}CD94^-$ NK cells activated with IL-1B and IL-23 (open histogram). Results of all are representative of >3 donors.

The HSC-derived NK cells were also compared to the $CD45^+CD3^-CD56^{+/-}CD117^+$ lymphoid fraction from tonsilar mononuclear cells. Like tonsilar cells, the HSC-derived stage III fraction showed high levels of NKp44, heterogeneous NKp46 expression, and lacked granzyme and perforin (FIG. 2a and not shown[6]). In contrast to tonsil, there was a remarkably high frequency of $CD117^{high}CD94^-$ cells. IL-22 producing NK cells in SLTs express IL-1 receptor (IL-1R)[1,13] and a significant proportion of the HSC-derived stage III cells also express this receptor (FIG. 2a). Interestingly, a minor fraction of HSC derived stage 1V cells ($CD56^{+/-}CD117^{low/-}CD94^+$) also expressed IL-1R, but did not produce IL-22 after IL-1β/IL-23 stimulation (FIG. 1E-F). Like stage III NK cells in tonsils, HSC-derived NK cells expressed CD161 and the lymph node homing receptor CCR6. The IL-7 receptor (CD127) was detected in tonsils, but not on HSC-differentiated cells. However, removal of IL-7 from the culture media for one week led to the detection of CD127 on a significant proportion of $CD56^{+/-}CD117^{high}CD94^-$ cells (FIG. 2a) suggesting that IL-7 down-regulates CD127 or occupied the CD127 epitope binding region.

Figures 2B, 2C:
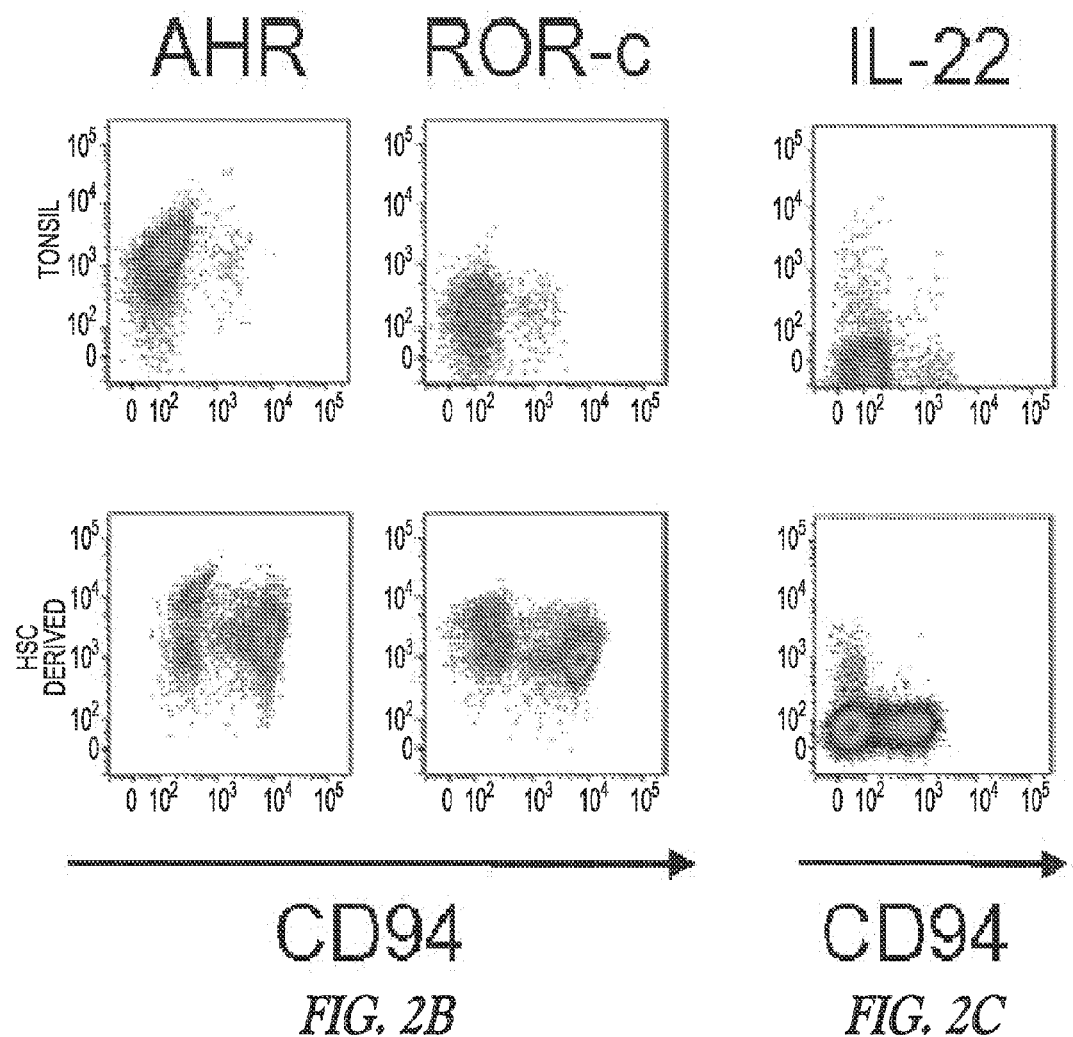
Figure 2D:
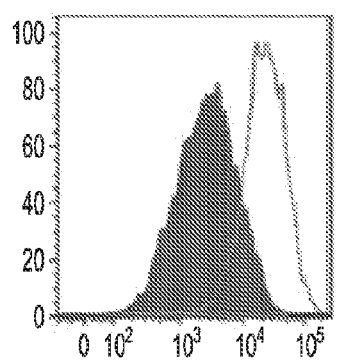

Similar to fresh tonsilar cells, HSC-derived $CD56^{+/-}CD117^{high}CD94^-$ cells showed high levels of the transcription factors AHR and ROR-γτ (FIG. 2b). Intracellular IL-22 was produced by $CD56^{+/-}CD117^{low/-}CD94^-$ cells from both sources, while it was absent in $CD56^{+/-}CD117^{low/-}CD94^+$ cells (FIG. 2c). To further characterize HSC-derived NK22 cells, supernatant from IL-1β/IL-23 activated cells were co-cultured with MSCs and an increase in ICAM expression on MSCs was observed (FIG. 2). To establish the potential yield of NK22 cells from these cultures, the NK22 cell population was defined as having a $CD56^{+/-}CD117^{high}CD94^-IL1R^+$ phenotype. Using this definition, a 1036+/−259 fold expansion from UCB $CD34^+$ progenitors was observed over 21-28 days of culture (n=4 donors).

One complexity in understanding IL-22 producing NK cells in humans is their location within SLT. This leads to difficulty in obtaining sufficient quantities of cells for study. It is speculated that through IL-22 elaboration, these cells play an important role in LN homeostasis and maintenance of mucosal barriers[4,14]. Following allogeneic hematopoietic cell transplantation, damage to SLT architecture occurs[15] and is associated with delayed immune reconstitution[16]. As well, GI tract injury has been implicated in graft vs. host disease induction through a cascade involving LPS translocation from the GI tract, resulting in accessory cell activation followed by IL-1 and TNF production (reviewed in[17]). In the SLT, stage III NK cells are in close proximity to dendritic cells that produce IL-1β[13]. Here a simple method leading to >1000× expansion of IL-22 producing NK lineage cells from HSCs is described. This is the first time that cells with functional properties previously described for NK22 and IL-22 producing stage III NK cells have been differentiated from HSC. This suggests that the NK22 cells and NK cells are tightly linked in ontogeny and that their final fate can be determined by cytokines encountered locally. Moreover, SLT is not required for their development. HSC-derived IL-22 producing NK cells will facilitate understanding of the lineage development these cells and has use for translational studies, including post-transplant adoptive transfer.

Bibliography
1. Crellin N K, et al. J Exp Med. 2010; 207:281-290.
2. Cupedo T, et al. Nat. Immunol. 2009; 10:66-74.
3. Hughes T, et al. Blood. 2009; 113:4008-4010.
4. Cella M, et al. Nature. 2009; 457:722-725.
5. Freud A G and Caligiuri M A. Immunol Rev. 2006; 214:56-72.
6. Grzywacz B, et al. Blood. 2006; 108:3824-3833.
7. Bachanova V, et al. 2009; 15:183-194.
8. Miller J S, et al. Blood. 1994; 83:2594-2601.
9. Miller J S, et al. Blood. 1999; 93:96-106.
10. McCullar V, et al. Exp Hematol. 2008; 36:598-608.
11. Freud A G, et al. Immunity. 2005; 22:295-304.
12. Maher D M, et al. J Histochem Cytochem. 2005; 53:631-642.
13. Hughes T, et al. Immunity. 2010; 32:803-814.
14. Trifari S and Spits H.201040:2369-2371.
15. Horny H P, et al. Blut. 1988; 57:31-40.
16. Kelly R M, et al. Blood. 2010; 115:1088-1097.
17. Reddy P and Ferrara J L. Blood Rev. 2003; 17:187-194.

Example II

Introduction

NK differentiation from hematopoietic progenitor cells (HPCs) can be studied in vitro[12-13]. This process depends on cytokines, notably IL-2 or IL-15, while other factors (SCF, FLT-3L) induce early HPC expansion and responsiveness to IL-2 and IL-15 signaling[14].

$CD34^+$ HPCs are heterogeneous and include cells at varying levels of differentiation. Multipotent HPCs with long-term repopulation potential are contained within the $CD34^+CD38^-$-subset[15]. More advanced lineage precursors, included in the $CD34^+CD38^+$ fraction[15], have been categorized as CMP ($CD34^+CD38^+CD123^+CD45RA^-$), GMP ($CD34^+CD38^+CD123^+CD45RA^+$) and MEP ($CD34^+CD38^+CD123^-CD45RA^-$)[28]. Subsets of $CD34^+$ precursors have also been distinguished by their ability to readily differentiate into NK cells. Surface receptors that define NK precursors include: $CD7^{13}$, $CD122^{16}$, $CD161^{17}$, integrin β7 and $CD45RA^{high\ 18}$.

Stromal cell layers have been used to differentiate HPCs into NK cells. Sources of stroma include bone marrow[13,19], murine fetal liver cell lines[20], and human splenic fibroblasts[21]. Stroma increases NK generation efficiency and advances the maturational status of HPC-derived NK cells[20]. Physiological concentrations of hydrocortisone (HDC) also advances NK cell development from $CD34^+$ HPCs[10].

Discrete stages of human NK cell differentiation were determined by studying $CD34^+$ cells cultured on the murine fetal liver stromal cell line, EL08.1D2[22]. Notably the stages we defined in vitro closely resemble those in human lymph nodes[23]. This culture system results in a strikingly high efficiency of NK cell differentiation from $CD34^+$ HPCs[22]. Herein the mechanism of stroma-induced NK cell differentiation is described to better understand the origins of NK cells. It is demonstrated herein that fetal liver stroma and HDC enhance NK differentiation by recruiting CMP and GMP to the NK lineage. Likewise, precursors at more advanced stages of myeloid differentiation retain NK cell generating capacity. The concept that NK cells can be derived from the myeloid lineage advances the understanding of NK ontogeny and the relationship to other blood lineages, creating the potential for therapeutic applications.

Materials & Methods $CD34^+$ Cells Isolation $CD34^+$ cells were positively selected from UCB mononuclear cells (Miltenyi biotech, CA). Selected cells were >97% pure and lacked CD56$^+$ cells (not shown). Where specified, CD34+ cells were FACS sorted into CD34$^+$NKlin$^+$, CD34$^+$CD38$^-$NKlin$^-$, CD34$^+$CD38$^+$NKlin$^-$ (NK lineage markers were defined as CD161, CD122, CD$^7$, Integrin β7 and CD45R$^{high}$; cells negative for all were considered NKlin$^-$). Granulo-monocytic precursors (CD34$^+$CD38$^+$CD64$^+$)[24], CMP (CD34$^+$CD38$^+$CD123$^+$CD45RA$^-$), and GMP (CD34$^+$CD38$^+$CD123$^+$CD45RA$^+$) were FACS purified from UCB CD34$^+$ cells.[25] Following the initial sort, the CMP and GMP fractions were re-sorted and deposited directly into culture wells at 1 or 10 cells per well.

NK Cell Differentiation Cultures

The embryonic liver cell line EL08.1D2 was cultured to confluence and irradiated (3,000 rads)[22]. CD34$^+$ cells or specified subsets were cultured with/without a monolayer of EL08.1D2 cells in Ham's F12+DMEM (1:2 ratio) with 20% human AB sera, ethanolamine (50 μmol/L), ascorbic acid (20 mg/L), 5 μg/L sodium selenite ($Na_2SeO_3$), β-mercaptoethanol (24 μmol/L), and penicillin (100 U/ml)-streptomycin (100 U/ml). At the start of cultures, IL-3 (5 ng/ml), IL-7 (20 ng/ml), IL-15 (10 ng/ml), SCF (20 ng/ml), FLT-3L (10 ng/ml) were added. Where specified, hydrocortisone (HDC) ($10^{-6}$M) (Stem Cell Technologies), M-CSF or DKK-1 (R&D systems, Minneapolis, Minn.) were added. Cultures were re-fed weekly by 50% volume change of media, supplemented with the above cytokines (except IL-3), with or without HDC. After 14, 21 and 28 days of culture, 3 replicate wells were harvested, counted and analyzed.

NKp Frequency Assay

CD34$^+$ HPC or specified subsets were plated at 200, 100, 50, and 25 cells/well, 24 replicates/dilution. Conditions included media +/−stroma (EL08.1D2) and +/−HDC ($10^{-6}$M). After 4 weeks cellular outgrowth was scored and split-well analysis was performed where half of each well was tested for K562 cytotoxicity. If cytotoxicity exceeded a predetermined cut-off value (mean spontaneous release+3× SD) wells were considered positive. The fraction of negative wells at each dilution was used to calculate the NKp frequency as determined by Poisson kinetics[26].

CMP and GMP Cultures

CMP and GMP (n=5) were double sorted and deposited at 1- and 10 cells per well (n=60 replicates per condition). Conditions included: (1) cytokines, (2) cytokines+stroma, (3) cytokines+stroma+HDC, and (4) methylcellulose enriched with growth factors (MethoCult, Stem Cell Technologies, Vancouver). The latter condition was included to control for their colony-generating potential (CMP or GMP). Cultures were maintained for 17-21 days then tested for expression of NK cell markers (CD56, CD94) in combination with myeloid markers (CD15, CD14, CD33). The colony forming potential of sorted fractions was assessed after 14-21 days of methylocellulose culture by two researchers, including an independent (blinded) investigator not otherwise involved in the study.

Methylocellulose Assay and Myeloid Cell Culture

CD34$^+$ HPCs were plated at 1 cell/well in methylocellulose enriched with growth factors (MethoCult GF+H4435, Stem Cell Technologies). After 20-21 days individual granulocyte-macrophage colonies (CFU-GM) were isolated and plated into culture in medium as for NK differentiation (IL-15, IL-7, SCF, FLT-3L) with stromal cells and HDC ($10^{-6}$ M).

Isolation of CD13$^+$ and M-CSFIce Cells

NK differentiation cultures were harvested after 14 days and depleted of CD56$^+$ cells using MACS beads. This CD56$^-$ population was FASC sorted into CD56$^-$CD33$^{+/-}$CD13$^{low/-}$, CD56$^-$CD33$^+$CD13$^{intermediate}$ and CD56$^-$CD33$^+$CD13$^{high}$ fractions. Sorted populations were cultured (in triplicates) at 10,000 cells/well in 96-well plates in NK differentiation medium +/−stroma and +/−HDC. After 18-21 days cells were analyzed. Similarly, CD34$^+$ cultures were harvested at d+18, CD56$^+$ cell were depleted and CD117$^+$ cells were isolated from CD56$^-$ fraction using MACS beads. The resulting populations were then FACS purified into CD56$^-$CD94$^-$CD117$^+$M-CSFR$^+$ (myeloid precursors) and CD56$^-$CD94$^-$CD117$^+$M-CSFR$^-$. (non-myeloid precursors, presumed to include lymphoid precursors) Sorted fractions were cultured as above. In selected experiments M-CSF was added.

FACS Analysis

The following antibodies were used: CD7-FITC, CD13-PE, CD1aFITC, CD14-FITC or PE, CD16 (FITC, PE or PerCpCy5.5), CD33 PerCpCy5.5, CD34 (Percp, PE and APC), CD38-APC, CD56-APC, CD94-FITC, CD117 (PE or PercpCy5.5), CD122-PE, CD161 (FITC or PE), CD158a-PE, CD158b-PE, and, CD158e-PE (DX-9), CD64-PE, Granzyme-B-FITC, Perforin-FITC, CD68 (macrosialin)-PE and myeloperoxidase-FITC. For CMP, GMP and MEP subsets CD123-PE, CD34-PerCp-Cy5.5, CD45RA-Horizon450 (all from BD Biosciences, CA), CD38-APC and Lineage cocktail including FITC conjugated CD2, CD3, CD4, CD7, CD8, CD10, CD14, CD16, CD19, CD11b, CD20, CD56, GPA, (e-Bioscience). Additional antibodies included: CD115-PE, CD45RA-FITC (Biolegend), CD13-FITC (Serotec, UK), lyzozyme-FITC (Caltag), NKp30-PE, NKp44-PE, and NKp46-PE (Beckman Coulter). Intracellular staining was performed using cytofix/cytoperm (BD Biosciences). FACS was performed on a FACS Calibur. Data was analyzed using WinMDI or FlowJo. Sorting was performed on FACSaria and post-sort reanalysis usually showed >99% purity (not shown).

$^{51}$Cr release assay. K562 or B721.221 lymphoblastoid cell line targets were used in killing assays[22].

Statistical Analysis: For grouped analysis, experimental values were normalized by log transformation before one (or two) way ANOVA, as indicated. Individual groups were compared with Bonferroni post test. Chi-square analysis was used to compare fractions of methylcellulose (CFU-GM) colonies that gave rise to NK cells.

Results

Stromal Cells and HDC Additively Enhance NK Cell Differentiation

Figure 3A:
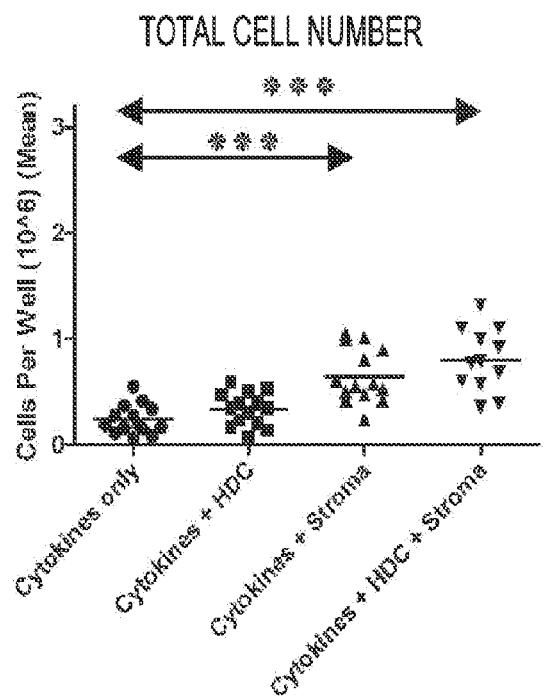
FIGS. 3A-F: HDC and stroma increase the number of NK cells generated from $CD34^+$ HPC. 500 $CD34^+$ cells were plated/well in 24-well cell culture plates. Where indicated, plates were previously coated with stromal cells (EL08.1D2) and irradiated (30 Gy). Where indicated, HDC ($10^{-6}$ M) was added to the starting, as well as, refreshing medium (added weekly). Average number of viable cells/well (of 3 replicates) after: (a) 14, (b) 21 and (c) 28 days of culture. Percentage of $CD56^+$ cells (by FACS) after: (d) 14, (e) 21 and (f) 28 days. Horizontal bars represent the means of 12 separate donors in various conditions. Groups showing significant differences in comparison with the "cytokines alone" group are indicated by asterisks (* $p<0.001$;  $p=0.001-0.01$; * $p=0.01-0.05$), as determined by repeated measures ANOVA on log transformed values with Bonferroni post-test.
Figure 3B:
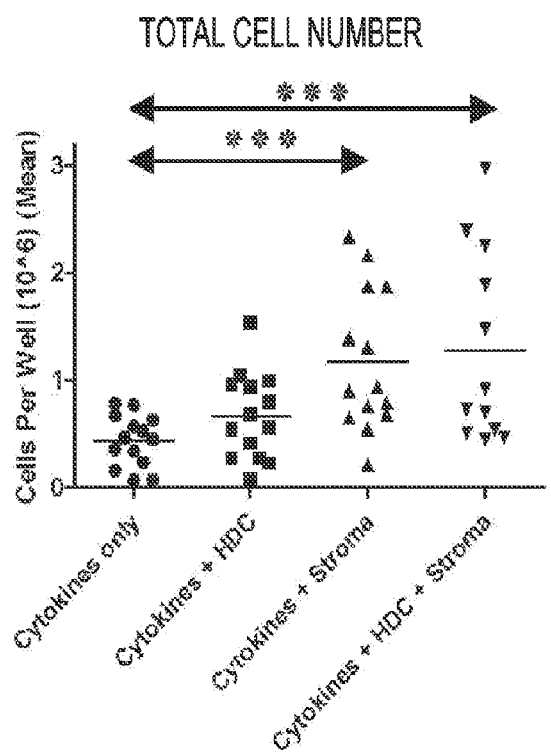
Figure 3C:
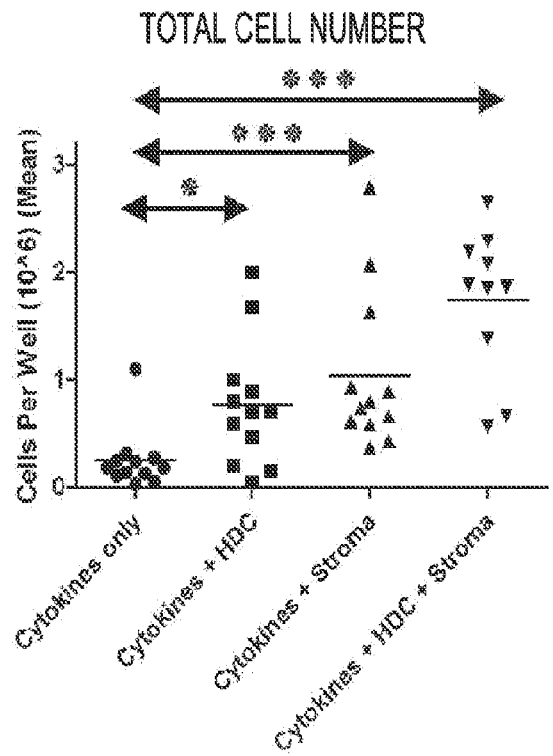
Figure 3D:
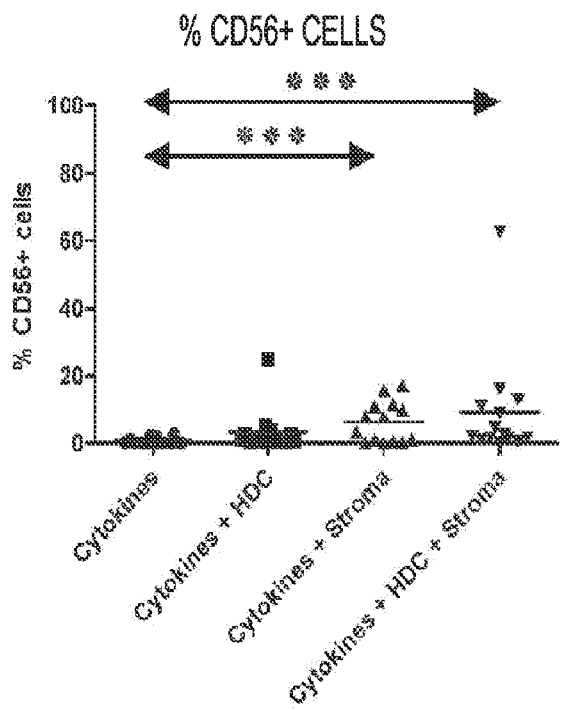
Figure 3E:
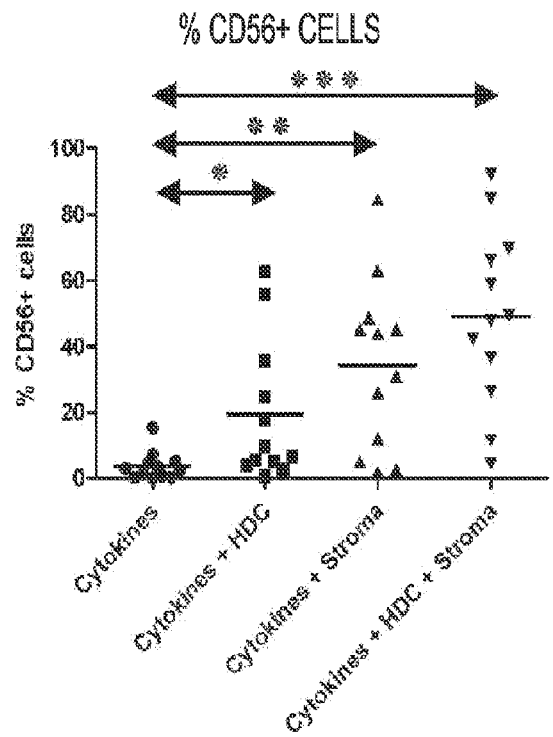
Figure 3F:
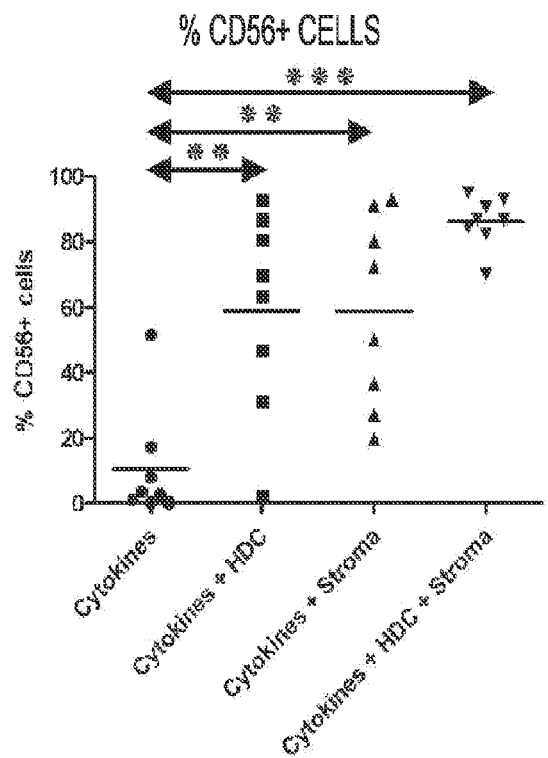

We investigated how stroma, HDC and the combination of the two impact NK differentiation. CD34$^+$ cells were cultured in media containing cytokines (defined here as, IL-3 for the first week, SCF, FLT-3L, IL-7 and -15) and for comparison, cells were cultured with: (1) cytokines and stroma, (2) cytokines and HDC or (3) the combination of all three. The addition of stroma and/or HDC significantly increased cell numbers and the percentage of NK cells (CD56$^+$ cells) at 2 (FIG. 3A, D), 3 (FIG. 3 B, E) and 4 (FIG. 3 C, F) weeks (p<0.05). The two factors (stroma and HDC) were additive since the combination was significantly better than either one alone (p<0.05 at 4 weeks).

With the addition of either HDC or stroma, all wells contained NK cells (not shown). However, when CD34$^+$ HPCs were cultured without stroma or HDC, considerable variability between replicates was observed. For instance, there were individual wells where NK cells developed, while in others they did not. This suggested that the CD34$^+$ HPC fraction contained precursors capable of NK differentiation with cytokines alone (i.e., without HDC or stroma). Given the well-to-well variability with initial input of 500 CD34$^+$ cells/well, such NK precursors appear to be rare. At least two non-exclusive mechanisms can explain these findings. First, HDC and stroma might increase the efficiency of NK cell generation from progenitors already "committed" to the NK lineage. Secondly, they might act upon progenitors that might not otherwise become NK cells. One method to verify if the latter possibility was operational is to measure the NK cell precursor frequency (NKp) using a limiting dilution assay (LDA). If stroma and/or HDC increase the frequency of $CD34^+$ HPC giving rise to NK cells in LDAs, then the logical explanation would be that these factors act on $CD34^+$ HPCs to recruit them to the NK lineage.

NKp Frequency in UCB-Derived $CD34^+$ Cells

Figure 4A:
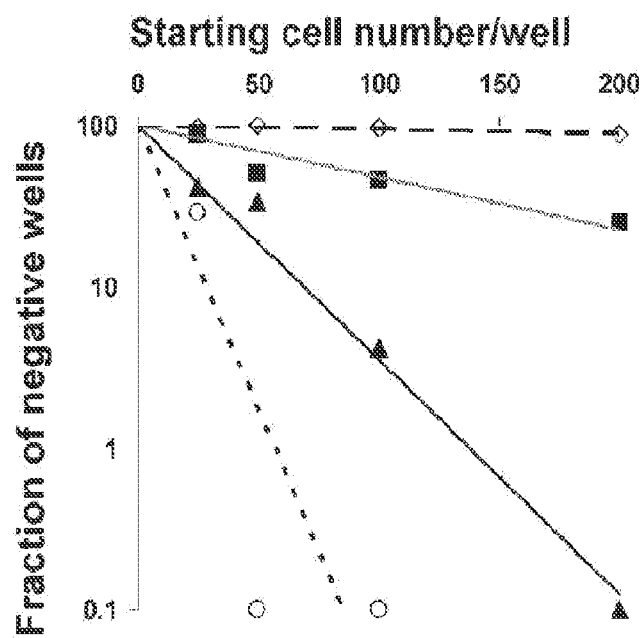
FIGS. 4A-C: EL08.1D2 stroma and HDC increase the NK precursor frequency (NKp) in the $CD34^+$ UCB fraction. (a) Semi-log plot presenting the results of a limiting dilution experiment with $CD34^+$ HPCs cultured in: cytokines alone (◇, long - dashed line), cytokines+HDC (■, grey line), cytokines+stroma (▲, black line) and cytokines+HDC+stroma (○, short-dashed line). Data for a single donor is shown and is representative of 8 donors tested. The steeper slope of regression line indicates increasing NKp frequency in different conditions. (8) NKp frequency/$10^6$ $CD34^+$ HPCs cultured in the above conditions (n=8 donors). Groups showing significant differences indicated by asterisks (* $p<0.001$;  $p=0.001-0.01$; * $p=0.01-0.05$), by repeated measures ANOVA on log transformed values with Bonferroni post-test. (C) Results of microscopic scoring of cell density in limiting dilution experiment at day +28. Each graph represents the results of a limiting dilution experiment using the same $CD34^+$ HPC cell suspension in different conditions (i.e. cytokines alone, cytokines+HDC, cytokines+stroma, cytokines+HDC+stroma). The total height of each bar represents 24 replicate wells at a given serial dilution (25 cells/well-200 cells/well). Each well was inspected using microscopy and cellular density was scored using a scale of 0 (no or very few cells) to 5 (densely populating the entire well). Results of a single representative donor is shown (n=8).
Figure 4B:
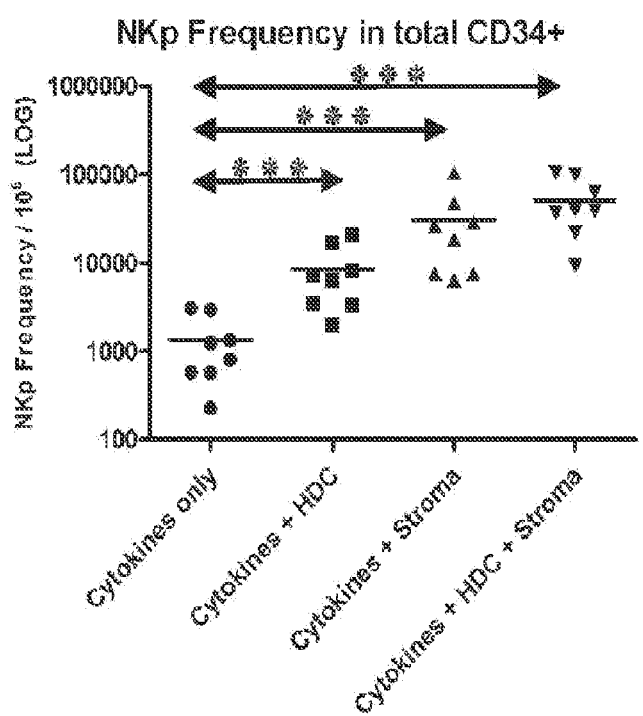

To measure the NKp frequency serial, two-fold dilutions of $CD34^+$ cells (200-250 cells/well, 24 replicates/dilution) were plated under the above conditions (cytokines alone, cytokines+stroma, cytokines+HDC, and cytokines+HDC+ stroma). Since the hallmark NK characteristic is unprimed effector function (e.g. K562 cytotoxicity), an NKp was defined as a $CD34^+$ HPC that could give rise to effectors with K562 cytotoxicity at 4 weeks of culture. Wells showing no cytotoxicity were assumed to contain no NKps (i.e., precursors capable of NK cell development under the given condition). The fractions of wells showing no killing (FIG. 4a) were used to calculate the NKp frequency (FIG. 4b)[26]. Compared to $CD34^+$ HPCs cultured in cytokines alone, the same cell suspension cultured with stroma, HDC or the combination of both showed a higher NKp frequency ($p<0.001$, (n=8)) (FIG. 4b).

Figure 4C:
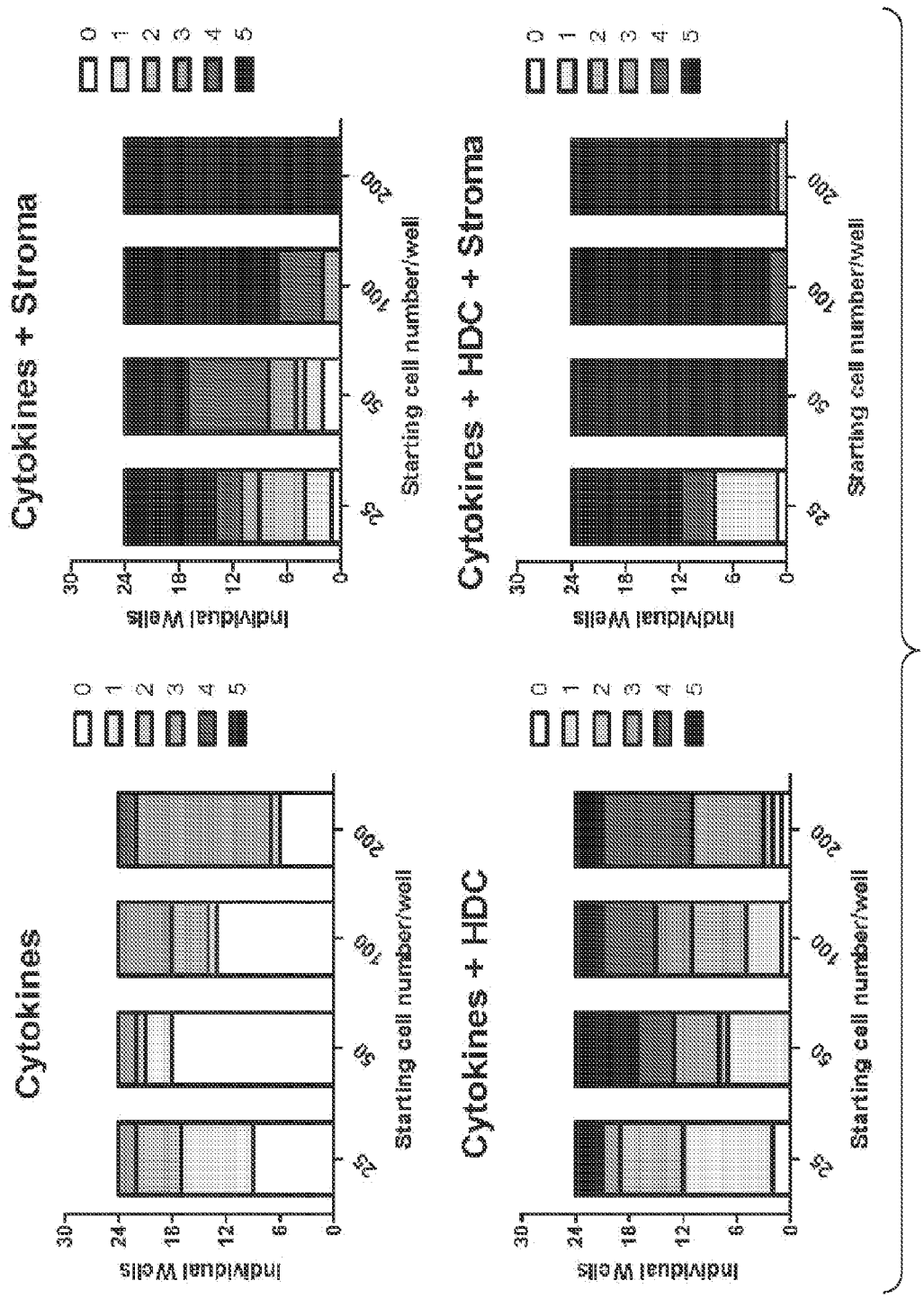

Before cytotoxicity testing, wells were microscopically scored for outgrowth. Similar to the NKp results, cell density was least when $CD34^+$ HPCs were cultured with only cytokines (FIG. 4c). Combining the cytotoxicity with the outgrowth data, wells with the following patterns were observed: 1) no (or few) cells and no cytotoxicity, 2) cells present, but no cytotoxicity and 3) cells present and cytotoxicity present. Representative wells were analyzed by FACS. Cytotoxicity was uniformly associated with the presence of NK cells at a functional stage of development (i.e., $CD56^{+/-}CD94^+CD117^{low/-}$)[22-23]. Frequently, these cells were intermixed with cells at earlier stages of development ($CD56^{+/-}CD94^- CD117^{high}$, not shown). Conversely, wells with no cytotoxicity lacked NK cells and instead contained cells of myeloid origin by FSS and SSC characteristics (not shown).

Collectively these studies demonstrate that a small, but measurable fraction of $CD34^+$ HPCs give rise to NK cells under the influence of only cytokines. Conversely, the majority of HPCs cultured with the above cytokine combination do not generate functional NK cells. Thus, the increased NKp frequency in the presence of stroma, HDC, or both, strongly suggest that these agents induce NK differentiation by acting upon HPCs (and their progeny), which do not generate NK cells when cultured with cytokines only.

Figure 5A:
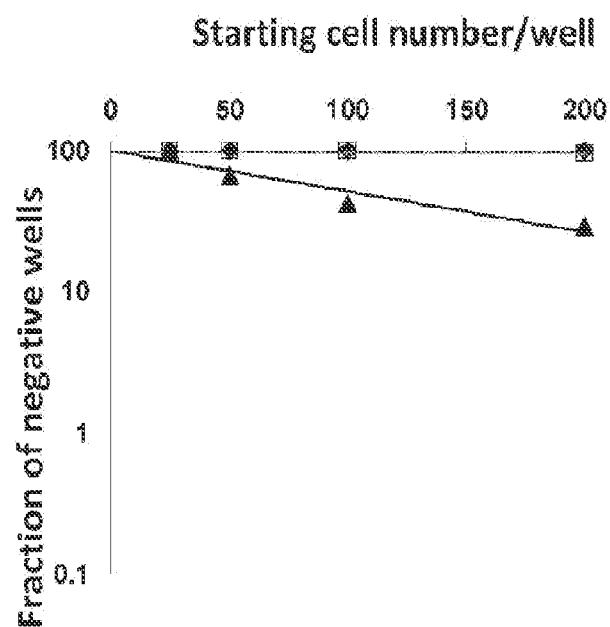
FIGS. 5A-H: Stroma and HDC induce NK differentiation in the $CD34^+$ HPC subset that could not differentiate into NK cells with cytokines alone. (A) Semi-log plot showing the fraction of negative wells (wells containing no NK precursors) as a function of input cells/well. Three subsets of $CD34^+$ cells were tested in limiting dilution culture with only cytokines (IL-15, IL-7, SCF, FLT-3L and IL-3): $CD34^+CD38^-NKlin^-$ (□, dashed line), $CD34^+CD38^+NKlin^-$ (◇, dotted line) and CD34+NKlin+ (▲, solid line). No positive wells were observed for NKlin⁻ subsets cultured with cytokines alone, and the plot therefore shows a flat slope for these conditions. In contrast, $CD34^+NKlin^+$ subset showed a measurable fraction of positive wells in culture with cytokines alone, thus creating a steeper slope of the regression line. A representative donor (n=4) is shown. (B) Calculated NKp frequencies for the three $CD34^+$ HPC subsets cultured with the above cytokines (n=4 donors), expressed as number of NKp/$10^6$ cells. (C) Semi-log plot of the fraction of negative wells as a function of input cells/well for the $CD34^+CD38^+NKlin^-$ fraction cultured with: cytokines alone (▲, long-dashed line), cytokines+HDC (■, grey line), cytokines+stroma (▲, black line) and cytokines+HDC+stroma (○, short-dashed line). A representative donor (n=4) is shown. (D) Calculated NKp/$10^6$ cells for $CD34^+CD38^+NKlin^-$ fraction cultured in different conditions (n=4 donors tested). (E) Semi-log plot of the fraction of negative wells as a function of input cells/well for the $CD34^+CD38^-NKlin^-$ fraction cultured with cytokines alone (◇, long-dashed line), with cytokines and HDC (■, grey line), with cytokines and stroma (▲, black line) and with cytokines+HDC+Stroma (○, short-dashed line). A representative donor (n=4) is shown. (F) NK precursor frequency per $10^6$ cells in the $CD34^+CD38^-NKlin^-$ population cultured in different conditions, n=4 donors tested. Groups showing significant differences indicated by asterisks (* $p<0.001$;  $p=0.001-0.01$; * $p=0.01-0.05$), one-way ANOVA on log transformed values with Bonferroni post-test. (G) Fold change in mRNA levels coding for TCF/LEF transcription factors and their downstream targets (WISP and CyclinD1) induced in NKlin⁻ $CD34^+$ HPCs after 14 days of culture of with: 1) cytokines, stromal cells and HDC vs. 2) cytokines only. (H) Effect of Dickkopf-1 (DKK-1) on the generation of NK cells from $CD34^+$ HPC in the culture with cytokines, stroma and HDC. Shown are the average number of $CD56^+$ cells/well after 21 days culture+/−SEM. The difference between no addition of DKK-1 and addition at 10 ng/ml is statistically significant $p=0.012$). Results are the mean of 6 wells for each condition and are representative of independent 2 donors.

Identification of $CD34^+$ HPCs that Require HDC or Stroma for In Vitro NK Cell Differentiation Several surface receptors are associated with NK lineage commitment, including CD7, CD122, CD161, integrin β7 and $CD45RA^{high}$ [13,16-18]. These were expressed on non-fully overlapping $CD34^+$ subsets (not shown). It was hypothesized that $CD34^+$ HPCs lacking all of these NK lineage markers ($CD34^+NKlin^-$) might be "uncommitted' to the NK lineage (i.e., unable to give rise to NK cells with cytokines alone). Two $NKlin^-$ subsets ($CD34^+CD38^-NKlin^-$, $CD34^+CD38^+NKlin^-$) were tested in the NKp frequency assay with- and without stroma and HDC. $CD34^+$ cells expressing any of the above NK lineage markers were used for comparison ($CD34^+NKlin^+$). In the absence of stroma and/or HDC, both $CD34^+NKlin^-$ populations ($CD38^-$ and $CD38^+$) yielded few wells with K562 cytotoxicity, resulting in a flat slope of the semi-log limiting dilution plot (FIG. 5a). In contrast, the $CD34^+NKlin^+$ population cultured in only cytokines produced a noticeable fraction of wells with K562 cytotoxicity, resulting in a steeper slope (FIG. 5a).

Figure 5B:
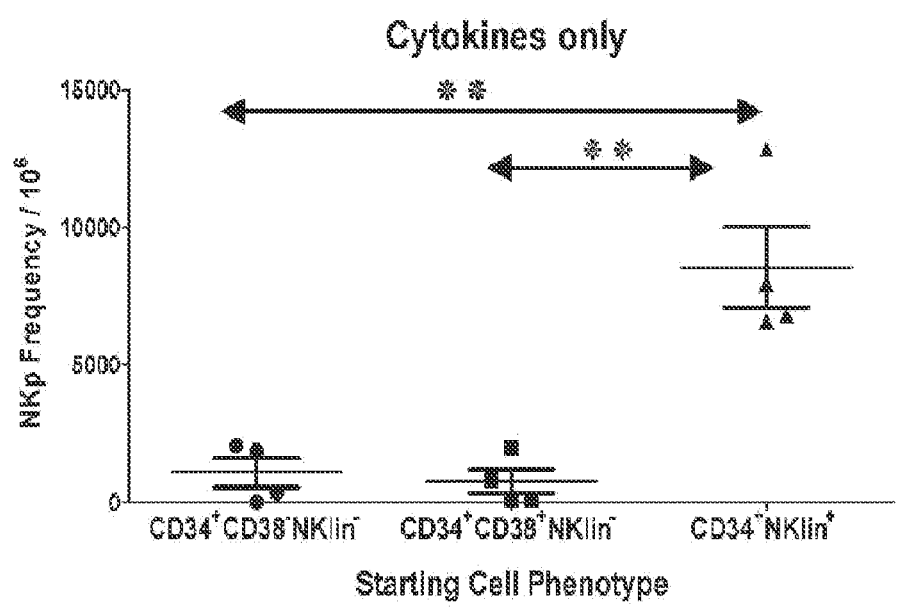
Figure 5C:
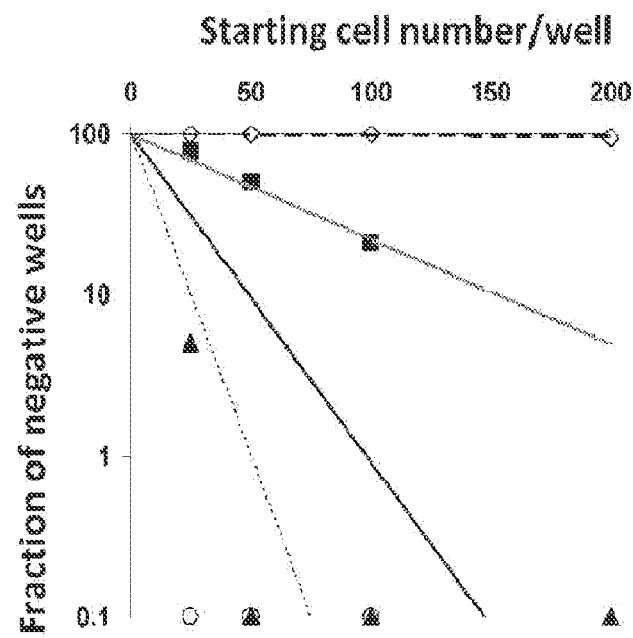
Figure 5D:
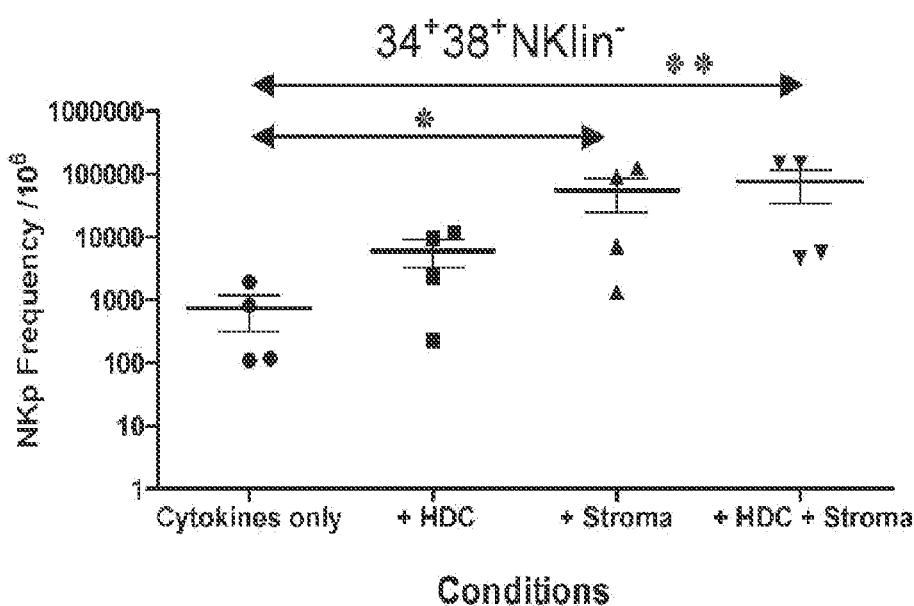
Figure 5E:
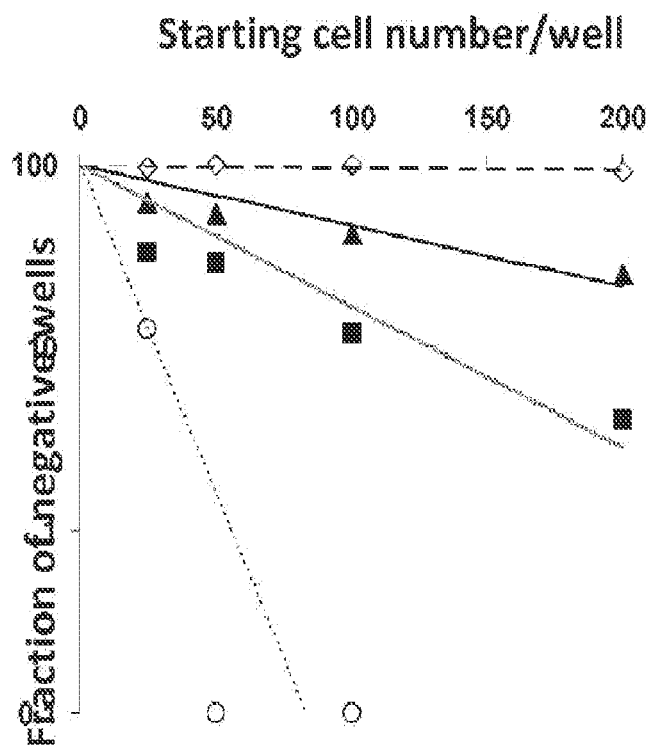
Figure 5F:
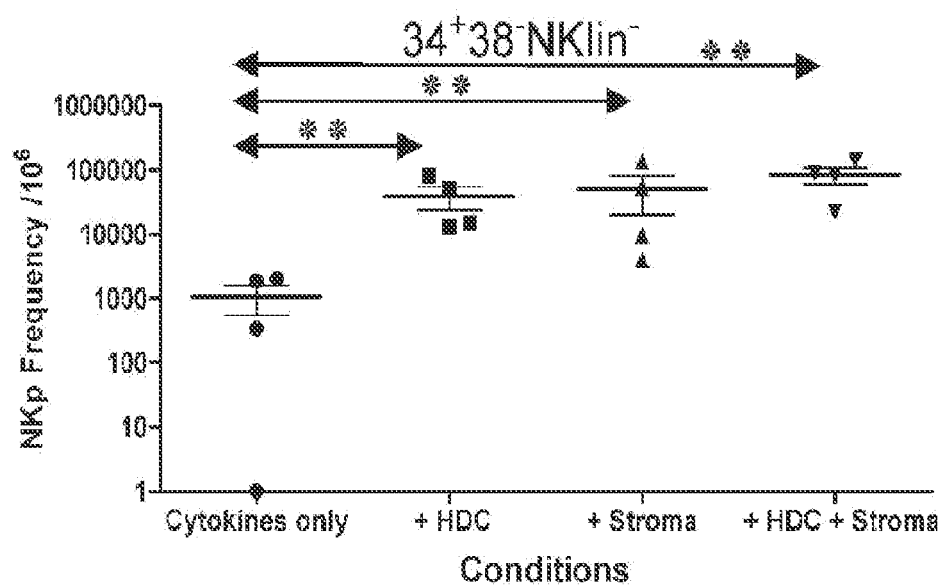

For the $NKlin^-$ populations ($CD38^-$ and $CD38^+$) the NKp frequency was not significantly different from 0 ($CD34^+CD38^-Nklin^-$: $1102/10^6$ cells, 95% CI (−598-2728); $CD34^+CD38^+NKlin^-$: $474/10^6$ cells, 95% CI (−637-2153)). In contrast, $CD34^+NKlin^+$ cells showed a higher NKp frequency (median: $7370/10^6$ cells, 95% CI (3891-13,178), n=4, $p<0.01$) (FIG. 5b). Addition of HDC and/or stroma induced the capacity of $CD34^+NKlin^-$ populations (both $CD38^-$ and $CD38^+$) to give rise to functional NK cells (FIG. 5 d, f), changing the slopes of the semi-log plots (FIG. 5 c, e). Thus, a subset of HPCs critically dependent on HDC and/or stroma to differentiate into NK cells (i.e. $CD34^+Nklin^-$) was defined.

Figure 5G:
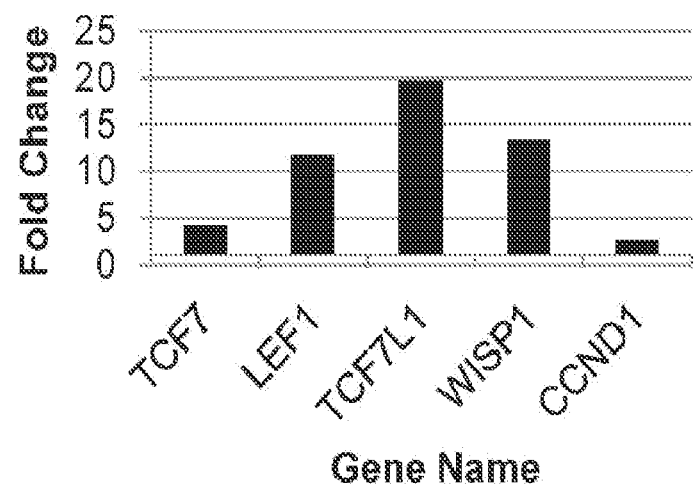
Figure 5H:
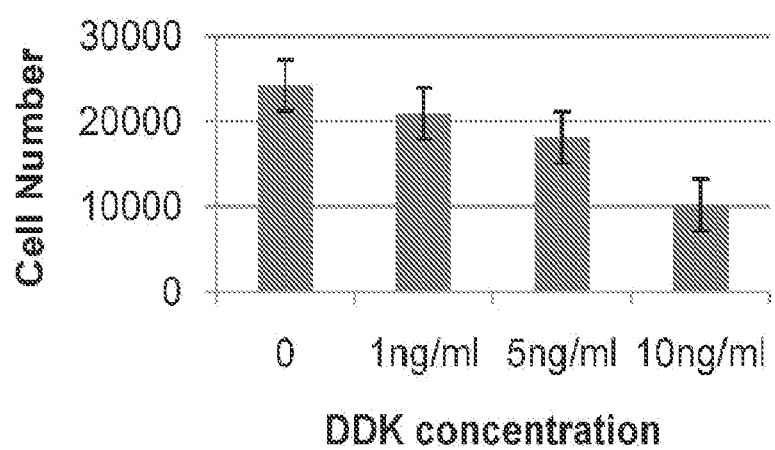

To understand the mechanisms of stroma and HDC, $CD34^+NKlin^-$ cells were cultured in cytokines or cytokines, stroma and HDC. Transcriptional profiling studies demonstrated upregulation of the WNT signaling pathway in response to stroma and HDC (FIG. 5G). To verify whether WNT signaling plays a role in the effect of stroma HDC, we added Dickkopf-1 (DKK-1), a canonical WNT pathway inhibitor, resulting in a dose-dependent decrease in the number of NK cells generated (p=0.012).

Figure 6A:
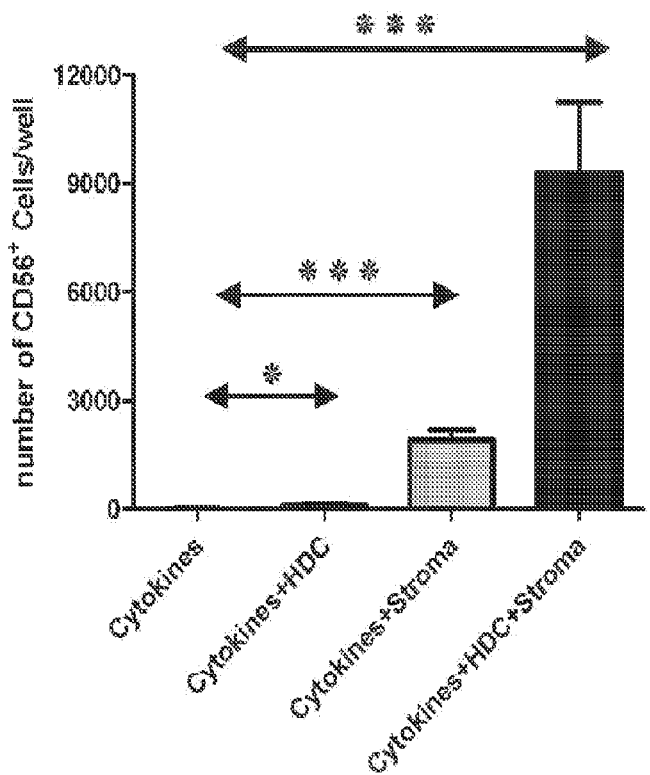
FIGS. 6A-C: Hydrocortisone and stroma induce $CD34^+CD38^-NKlin^-$ progenitors to become NK cells. (A) and (B) $CD34^+CD38^-NKlin^-$ cells were cultured at 100 cells/well in 12 replicates. After (A) 14 and (B) 21 days half the contents of each well were harvested and analyzed for the presence of $CD56^+$ cells by FACS (enumeration was performed with polystyrene beads). The average number of $CD56^+$ cells/well is presented. A representative donor is shown (n=4). Groups showing significant differences are indicated by asterisks (* $p<0.001$;  $p=0.001-0.01$; * $p=0.01-0.05$), one-way ANOVA on log transformed values with Bonferroni post-test. (C) Phenotype of cells derived from $CD34^+CD38^-NKlin^-$ cells under various conditions. Representative examples of individual wells after 14 days of culture with cytokines alone (IL-15, IL-7, SCF, FLT-3L, and IL-3, left), cytokines+HDC (second column), cytokines+stroma (third column) and cytokines+HDC+stroma (right).
Figure 6B:
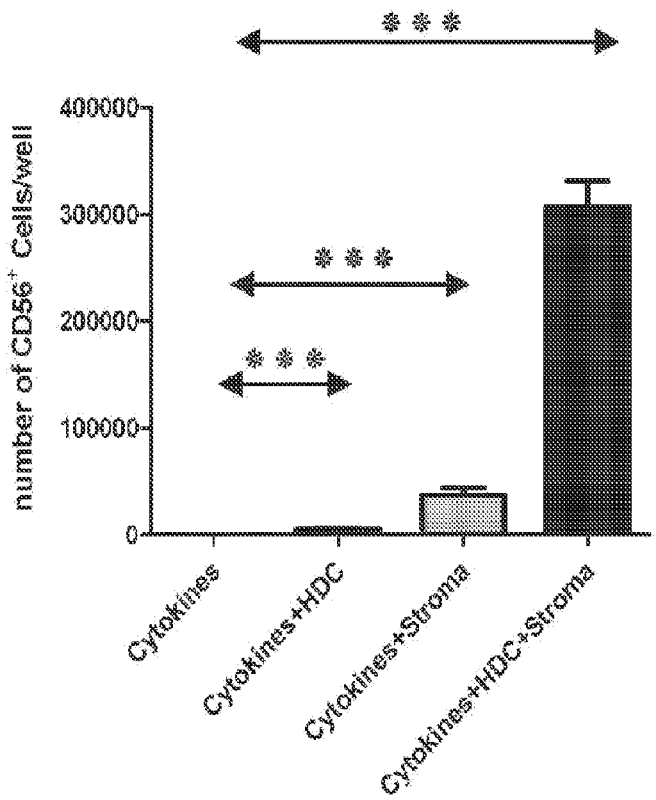

While the above NKp frequency assay has a functional end-point (i.e., cytotoxicity); it offers no insight into the developmental events over the 4 week culture. Prior studies show that HDC increases NK expansion[27] perhaps through proliferation or anti-apoptotic activity. Thus, HDC and/or stroma might simply induce proliferation or maintain survival of immature NK cells. To address this, cultures were evaluated at day +14 and +21. $CD34^+NKlin^+$ cells cultured in only cytokines (i.e., no stroma or HDC) generated $CD56^+$ NK cells within 14 days; whereas $CD34^+NKlin^-$ cells did not. In an alternative approach, small numbers of $CD34^+Nklin^-$ cells (100 cells/well, 12 replicates) were tested at day +14 and +21. In the presence of cytokines alone, $CD56^+$ cells were not observed. In contrast, HDC and/or stroma induced $CD56^+$ development after 14 and 21 days (FIG. 6a, 6b, respectively). Collectively these results demonstrate that $CD34^+NKlin^-$ cells did not develop into $CD56^+$ cells throughout the culture with cytokines alone, excluding the possibility that NK cells merely failed to expand and/or survive in the absence of HDC and/or stroma.

Figure 6C:
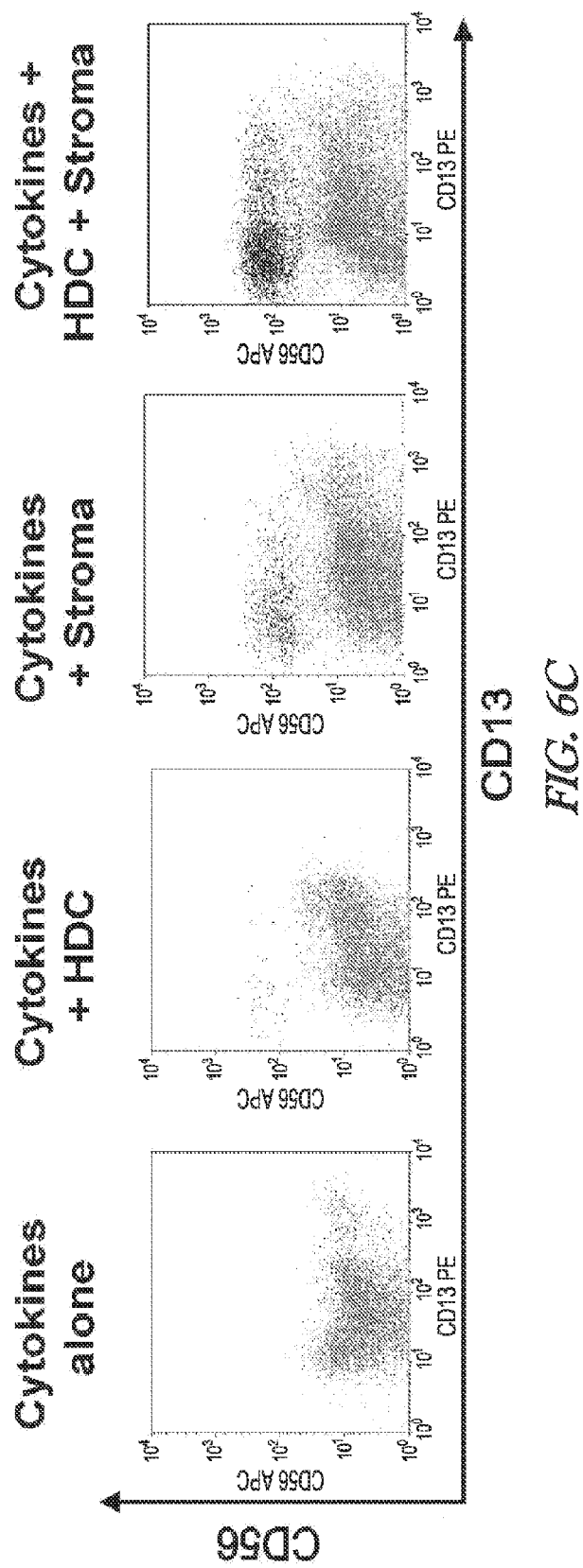

Transient myeloid antigen expression on developing NK cells $CD34^+NKlin^-$ cells cultured with only cytokines showed growth after 14 and 21 days, but did not differentiate into NK cells (FIG. 6c). The majority of these cells expressed markers associated with the myeloid lineage (CD13 and CD33) (FIG. 6c). When the same $CD34^+NKlin^-$ cells were cultured with HDC and/or stroma, some $CD56^+NK$ cells co-expressed CD13 and CD33 (FIG. 6c). Thus, CD56+ cells might arise from $CD13^+CD33^+$ precursors. Perhaps stroma and HDC can recruit myeloid progenitors to differentiate into NK cells.

Figure 7A:
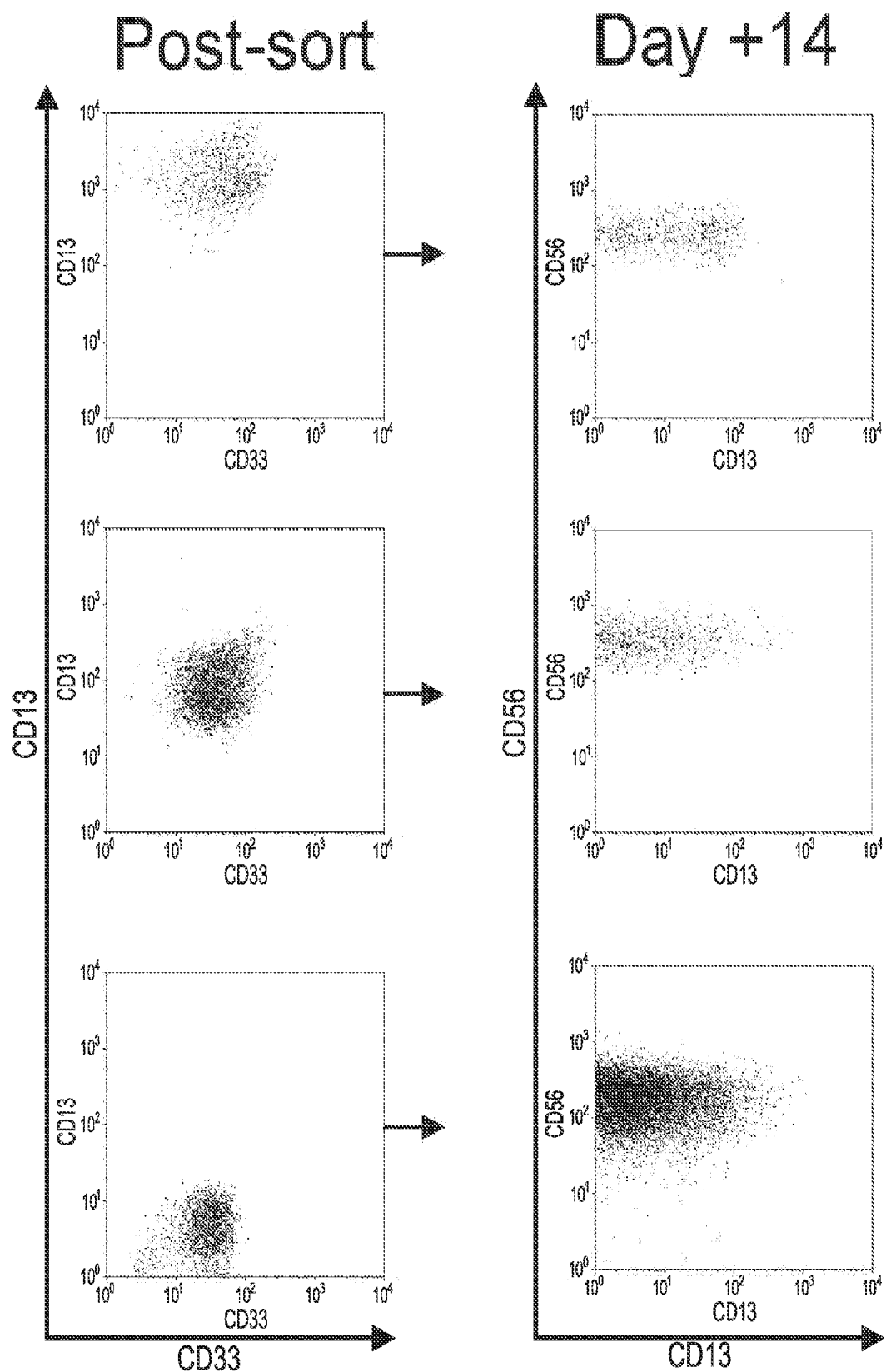
FIGS. 7A-C: $CD13^+CD56^-$ cells can give rise to NK cells. (A) Cells with distinct levels of CD13 expression: $CD13^{low/neg}$ (bottom), $CD13^{intermediate}$ (middle) and $CD13^{high}$ (top panel) were FACS purified from NK differentiation cultures (at day +14) and cultured further with cytokines and stroma. All three subsets gave rise to $CD56^+$ NK cells, some of which co-expressed CD13. (B) Quantitative yield of $CD56^+$ NK cells/$10^4$ FACS sorted $CD13^+$ cells. There was decreasing NK cell generation ability with increasing CD13 expression. A representative donor is shown (n=4). Groups showing significant differences indicated by asterisks (* p<0.001;  p=0.001-0.01; * p=0.01-0.05), one-way ANOVA on log transformed values with Bonferroni post-test. (C) Freshly isolated, GMPs (CD34$^+$CD38$^+$CD123$^+$CD45RA$^-$) were double sorted from UCB and deposited into 96 well plates with stroma, HDC and cytokines (FLT-3L, SCF, IL-7 and IL-15). After ~21 days progeny were analyzed by FACS. Shown are the cells falling within the lymphoid gate by FSS vs. SSC.
Figure 7C:
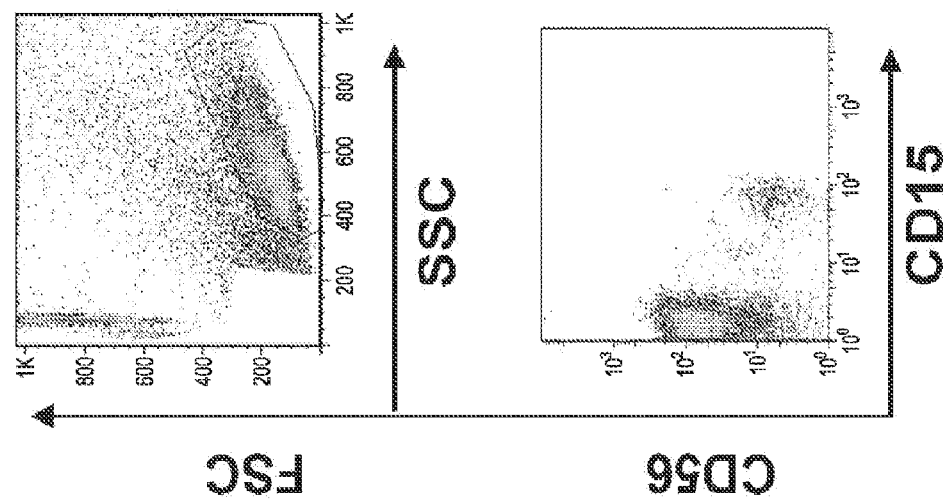
Figure 7B:
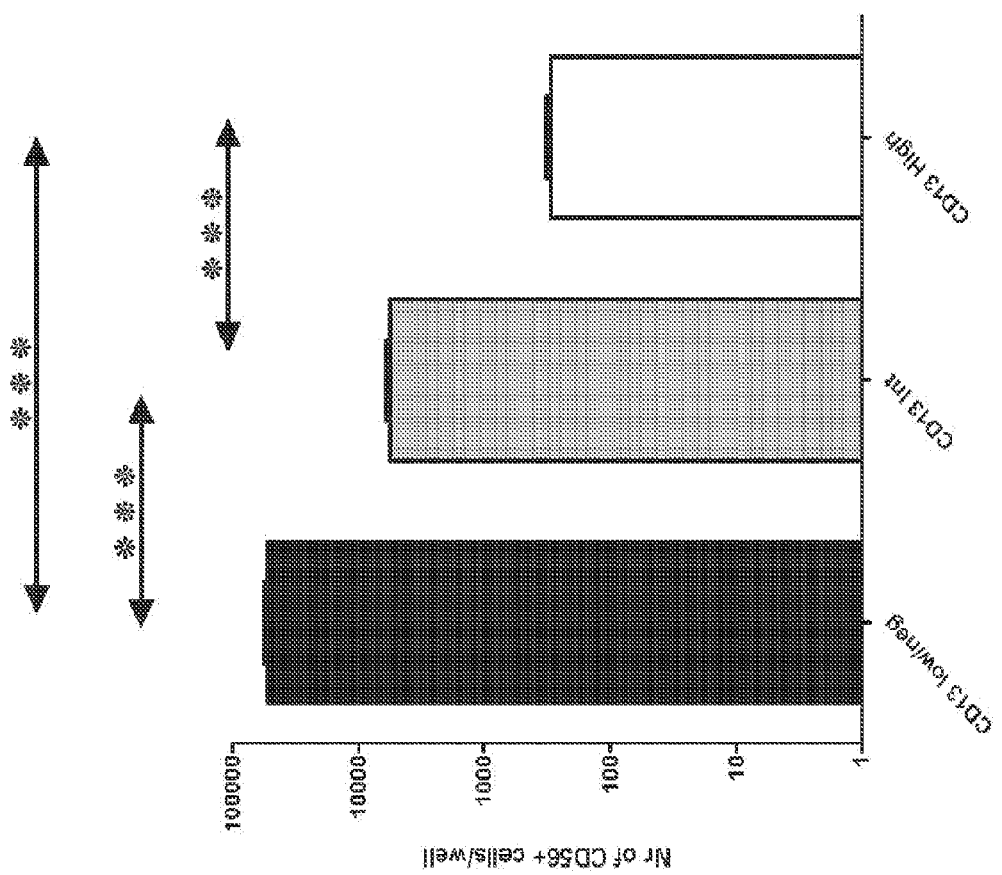

$CD13^+CD33^+$ cells in these cultures were tested for characteristics unique to the myeloid lineage. $CD13^+$ cells expressed intracellular enzymes (myeloperoxidase, lyzozyme, macrosialin (CD68)) and surface receptors (CD14, and CD1a) consistent with myeloid maturation. It was next tested whether precursors with varying amounts of CD13 could give rise to NK cells. Not only the CD13$^{low/-}$, but also the CD13$^{int}$ and CD13$^{high}$ subsets differentiated into NK cells after culture with cytokines and stroma (FIG. 7a). The efficiency of NK cell generation decreased with increasing CD13 expression (p<0.05) (FIG. 7b). Thus, cells following myeloid differentiation as indicated by increasing CD13 staining intensity[28], gradually lose the ability to give rise to NK cells.

Individual CFU-GM Colonies Give Rise to NK Cells Under the Influence of Stroma, HDC and Cytokines, but not Cytokines Alone To further test whether myeloid cells could give rise to NK cells, CD34$^+$ cells were plated in methylcellulose. Individual CFU-GM colonies were isolated and cultured in NK supporting conditions A fraction of CFU-GM colonies gave rise to NK cells (CD56$^+$ lymphocytes by FACS) after culture with cytokines, stroma and HDC, but not with cytokines alone (9 of 54 vs. 0 of 36, p=0.01).

In the Presence of HDC and/or Stroma, Freshly Isolated CMPs and GMPs can Develop into NK Cells Prior studies have identified human hematopoietic progenitors with capacity for myeloid and erythroid differentiation (CMPs: CD34$^+$CD38$^+$IL-3R$^{low}$CD45RA$^-$), as well as descendants that are restricted to the myeloid lineage (GMP: CD34$^+$CD38$^+$IL-3R$^{low}$CD45RA$^+$)[25]. It was examined whether freshly isolated CMPs and GMPs could develop into NK cells. Cells were double sorted directly into 96-well plates. As a control, CMPs and GMPs were also deposited into plates containing methylcellulose. As previously described[25], single CMPs gave rise to myeloid, erythroid or mixed (GEMM) colonies (cloning efficiency 61.7-91.7%, average 76.7%), while GMPs yielded exclusively myeloid colonies (cloning efficiency: 43.3-82.3, average 62.7%)) (FIG. 10) and none of the wells showed two separate colonies. GMP plated at 10 cells per well gave virtually no erythroid or mixed colonies (1 mixed colony in 300 wells, n=5 donors). When cultured in NK supporting cytokines (i.e., IL-3, SCF, FLT-3L, IL-7 and IL-15), CMPs and GMPs very rarely yielded CD56$^+$ cells (0.7% of wells, table 1). These CD56$^+$ cells were at an immature stage of NK differentiation (CD56$^{+/-1}$ $^{CD}$117$^{high}$CD94$^-$)[18,22] (not shown). When the same populations were cultured with cytokines+stroma+/−HDC, a significant fraction generated CD56$^+$ cells (FIG. 10). These CD56$^+$ cells fell in the lymphocytic gate, (by FSC/SSC) and co-expressed CD94, corresponding to mature, functional NK cells[18,22]. Myeloid cells (CD15$^+$) coexisted with NK cells in some cultures (FIG. 7C) demonstrating that a single CMP or GMP could produce both myeloid cells and NK cells. As in the above experiments, single CFU-GM colonies (derived from the control sorted CMP and GMPs cultured in methylocellulose) could give rise to NK cells if isolated and further cultured in cytokines+stroma+HDC (2 of 30 colonies, not shown). These results demonstrate that on a single-cell level, myeloid progenitors (CMPs and GMPs) can produce NK cells.

To reaffirm this conclusion, granulo-monocytic precursors were FACS purified according to an alternative definition[24]. CD34$^+$CD38$^+$CD64$^+$ myeloid precursors also differentiated into NK cells under the influence of cytokines and stroma with a frequency similar to the remaining CD34$^+$CD38$^+$ NKlin$^-$ precursors.

NK Cells Derived from Myeloid Precursors

Figure 8A:
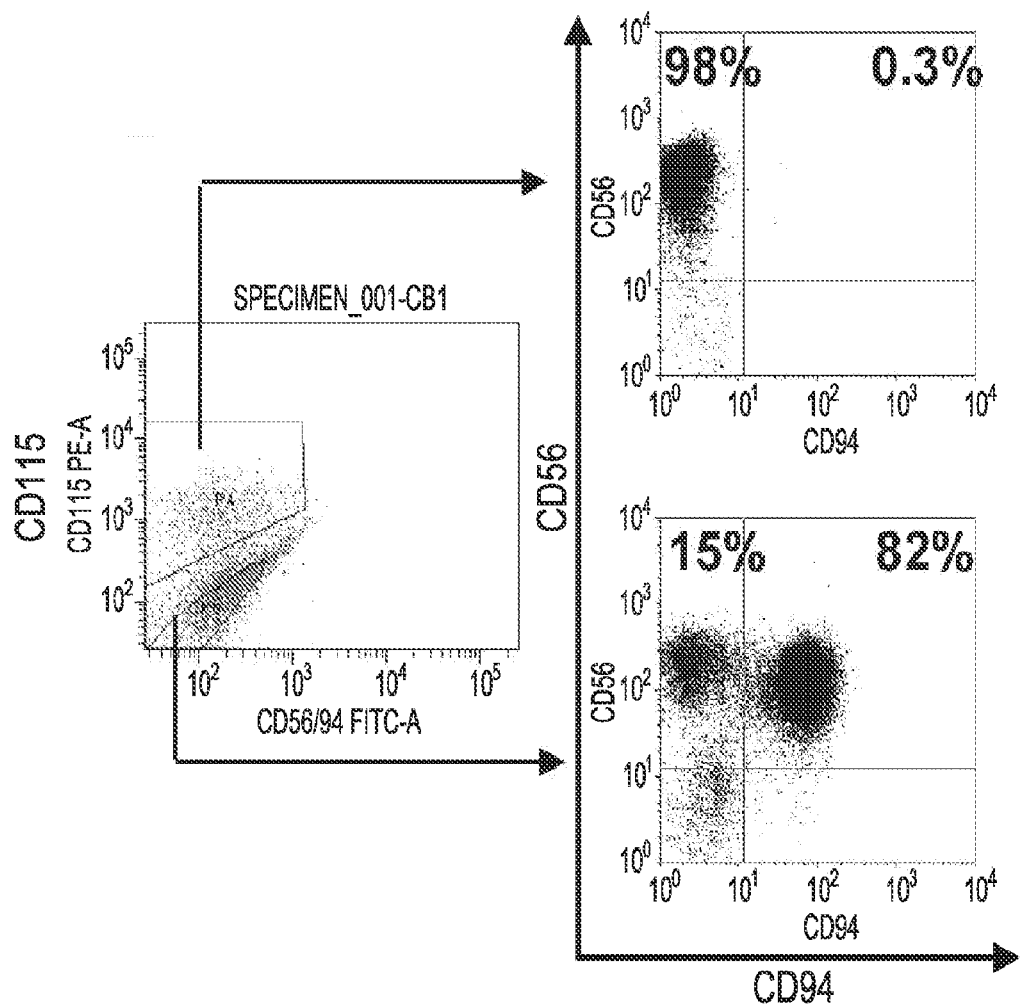
FIGS. 8A-E: M-CSFR$^+$ precursors can become NK cells, but have differential developmental requirements. (A) The CD56$^-$CD117$^+$ cell fraction was isolated from day +18 NK cell differentiation culture of CD34$^+$ cells and labeled for M-CSFR (CD115) expression. FACS sorting gates for the M-CSFR$^+$ and M-CSFR$^-$ subsets are shown. Upon further culture for 2 weeks with cytokines alone (IL-15, IL-7, SCF, FLT-3L) the M-CSFR$^+$ subset gives rise to CD56$^{+/-}$CD94$^-$ NK cells (upper plot), whereas M-CSFR" subset generates predominantly CD56$^{+/-}$CD94$^+$NK cells (lower plot). (B) Addition of HDC, stroma or both to CD56$^-$CD117$^+$M-CSFR$^+$ myeloid precursors induces increasing acquisition of CD94 (upper panel) and KIR (lower panel). (C) The CD56$^-$CD117$^+$M$^-$CSFR$^+$ subset generates increasing numbers of CD14$^+$ cells upon addition of M-CSF (white bars—No M-CSF, grey bars—10 ng/ml, black bars—50 ng/ml). The number of CD14$^+$ cells is shown after 1 week culture with NK supporting cytokines (IL-15, IL-7, SCF, FLT-3L)+stroma (left) or cytokines+stroma+HDC (right). (D) M-CSF at high doses abolishes NK cell development of CD56$^-$CD117+M-CSFR+ precursors. Shown are the number of CD56$^+$ cells when CD56$^-$CD117+M$^-$CSFR$^+$ precursors are cultured in NK supporting cytokines (IL-15, IL-7, SCF, FLT-3L)+stroma (left) or cytokines, stroma and HDC (right) and cultured with/without M-CSF (white bars—No M-CSF, grey bars—10 ng/ml, black bars—50 ng/ml). The number of NK cells at 2 weeks is shown. (E) The CD56$^-$CD117$^+$M-CSFR$^+$ subset cultured with low concentrations (0, 1, 10 and 20 ng/ml) of M-CSF induces CD56$^+$NK cells with co-expression of CD14 (percentages CD14$^+$ in CD56$^+$ fraction indicated). Cells were present in the lymphocyte gate by SSC vs. FSC characteristics (not shown). Groups showing significant differences indicated by asterisks (* p<0.001;  p=0.001-0.01; * p=0.01-0.05), two-way ANOVA on log transformed values with Bonferroni post-test.
Figure 8B:
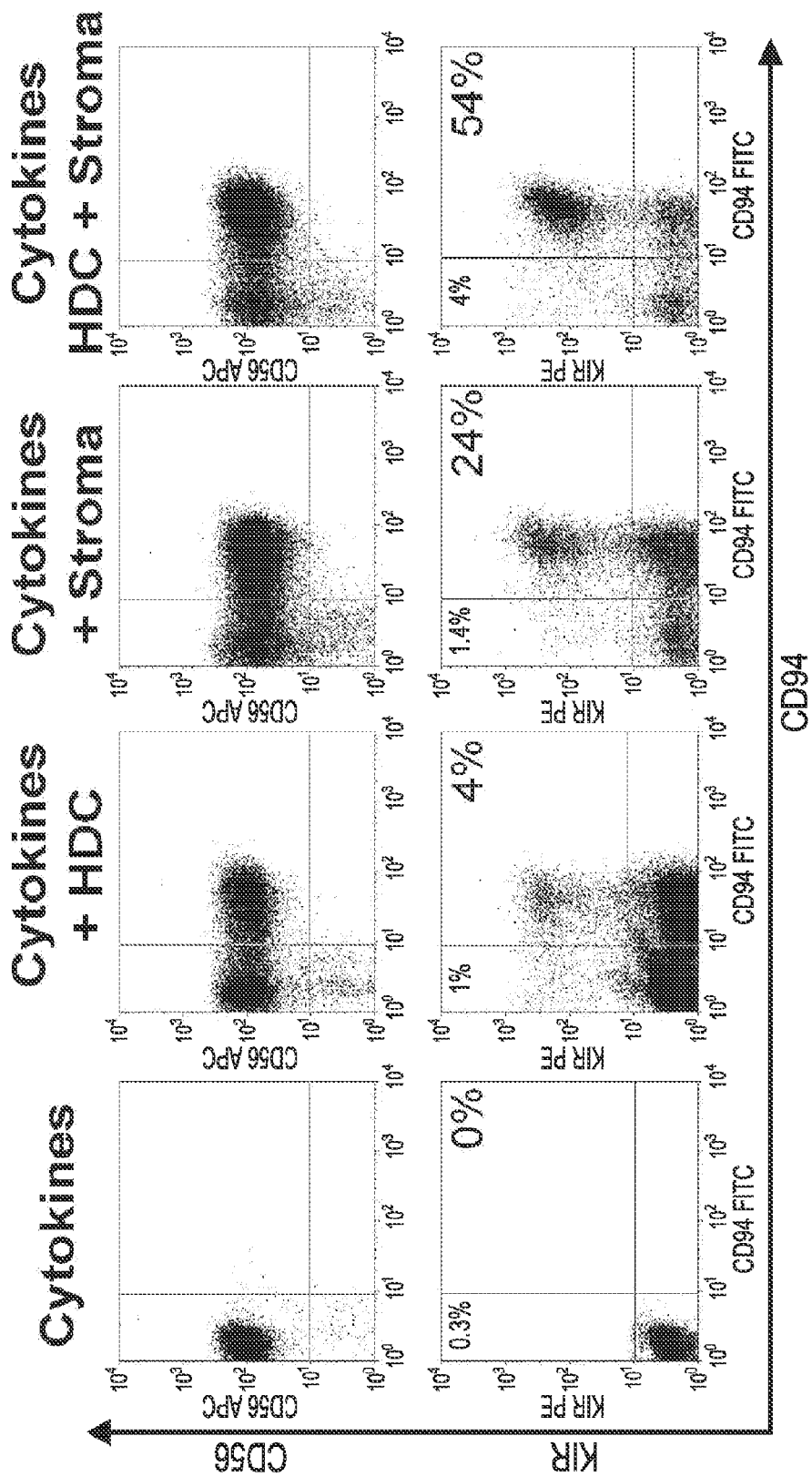

Next, myeloid progenitors were isolated on the basis of M-CSF receptor expression. The M-CSF receptor (M-CSFR, CSF-1R, CD115) is expressed by granulomonocytic precursors[29] and renders hematopoietic cells responsive to M-CSF, a growth factor promoting monocytic differentiation[30]. Therefore, M-CSFR is not merely a phenotypic marker, but is functionally linked to the monocytic lineage. It was previously determined that CD34$^+$ HPCs cultured on stroma continue to generate NK cells when depleted of CD56$^+$ cells after 2-3 weeks culture. The cells responsible for this are contained in the CD56$^-$CD117$^+$ subset ([22] and not shown). These cells variably express M-CSFR (FIG. 6a). Therefore, CD56$^-$CD117$^+$M-CSFR$^+$ and CD56$^-$CD117$^+$M-CSFR-cells were isolated from NK differentiation cultures to test their potential to generate NK cells. Both populations gave rise to CD56$^+$ cells upon further culture (FIG. 8a). To examine their maturation status, cells were tested for CD94 expression[22-23]. CD56$^-$CD117$^+$M-CSFR-precursors cultured in only cytokines readily differentiated into functional NK cells (CD56$^{+/-}$CD94$^+$). In contrast, CD56$^-$CD117$^+$M-CSFR$^+$ precursors cultured in cytokines alone gave rise to CD56$^+$ cells lacking CD94 (FIG. 8a). Addition of HDC and/or stroma to CD56$^-$CD117$^+$M-CSFR$^+$ myeloid precursors increased the CD94 and KIR expressing cells (FIG. 8b). Thus, CD56$^-$CD117$^+$M-CSFR$^+$ myeloid precursors require HDC and/or stroma to advance to a functional stage of NK differentiation, while the M-CSFB$^-$ counterparts do not.

Figure 8C:
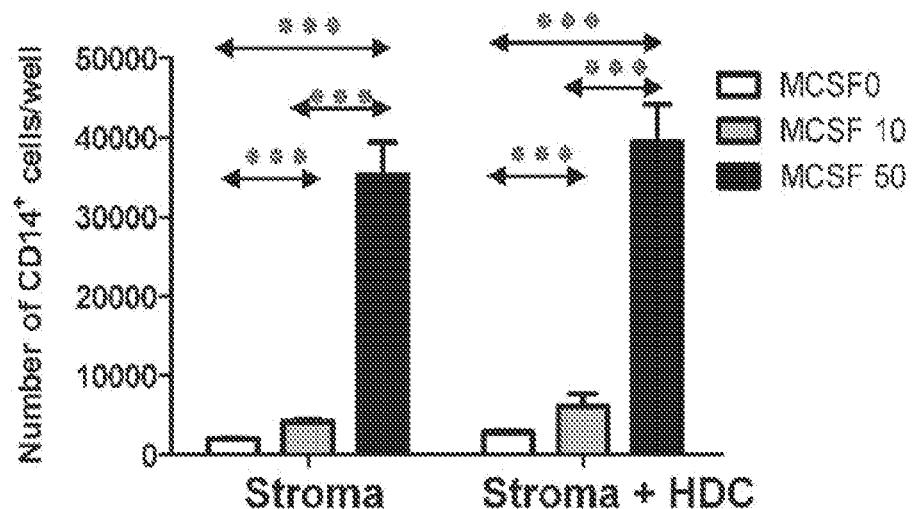
Figure 8D:
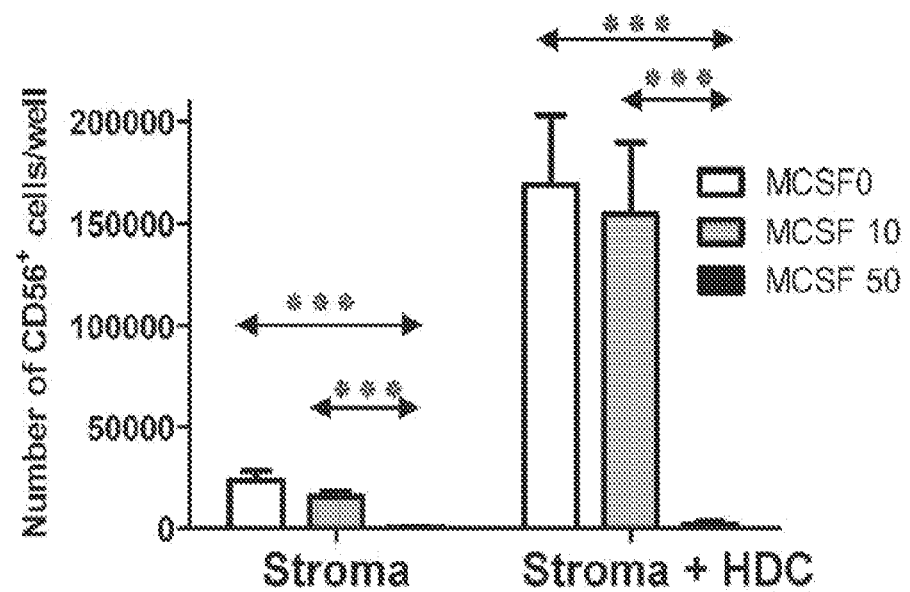
Figure 8E:
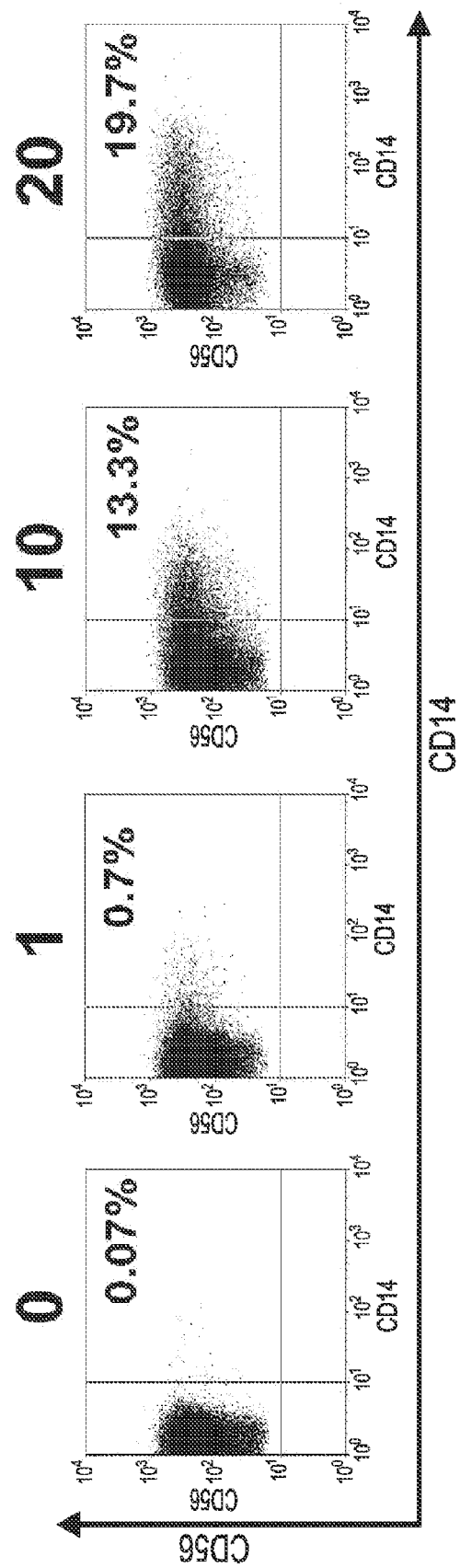

To investigate whether myeloid and NK differentiation represent two alternative developmental pathways for CD56$^-$CD117$^+$M-CSFR$^+$ precursors, M-CSF was added to NK developmental cultures. M-CSF increased the generation of CD14$^+$(CD56$^-$) monocytes and decreased NK cell development in a dose dependent manner (p<0.001) (FIGS. 8c and d, respectively). High concentrations of M-CSF (>50 ng/ml) abolished NK cell development from M-CSFR$^+$ precursors, despite conditions optimal for NK cell development (cytokines, stromal cells and HDC) (FIG. 8d). Thus, development of NK cells (CD56$^+$) or monocytes (CD14$^+$ CD56$^-$) from M-CSFR expressing myeloid precursors are alternative outcomes, influenced by M-CSF. Interestingly, at lower concentrations (1-20 ng/ml), M-CSF induced low-level CD14 co-expression on a fraction of developing CD56$^+$ lymphocytes (FIG. 8e). This provides complementary evidence that the cells that give rise to NK cells also respond to M-CSF. Collectively, these studies show that myeloid progenitors can generate NK cells, strongly supporting a myeloid NK cell differentiation pathway.

Distinct properties of myeloid precursor-derived NK cells

Figure 9A:
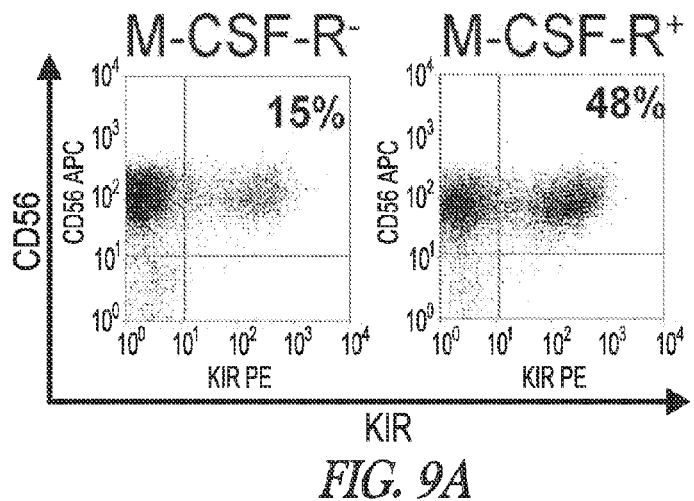
FIGS. 9A-E: NK cells derived from myeloid (M-CSFR$^+$) precursors show abundant KIR expression and higher cytotoxicity compared with lymphoid (M-CSFR$^-$) precursors. (A) Expression of KIR (combination of CD158a, CD158b and CD158e1) is higher on NK cells derived from myeloid (M-CSFR$^+$) precursors (right), compared to M-CSFR$^-$ derived NK cells (left). A representative donor is shown (n=4). (8) Percentages of KIR$^+$ NK cells derived from CD56$^-$CD117$^+$M-CSFR$^+$ (empty triangles) and CD56$^-$CD117$^+$M-CSFR$^-$ (full circles) progenitors for 4 individual donors are shown (Mean+/−SEM, >3 replicates for each donor).
Figure 9B:
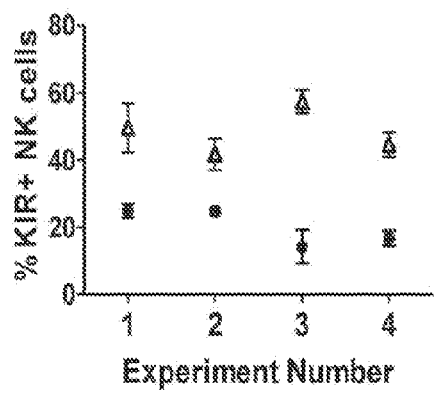
Figure 9C:
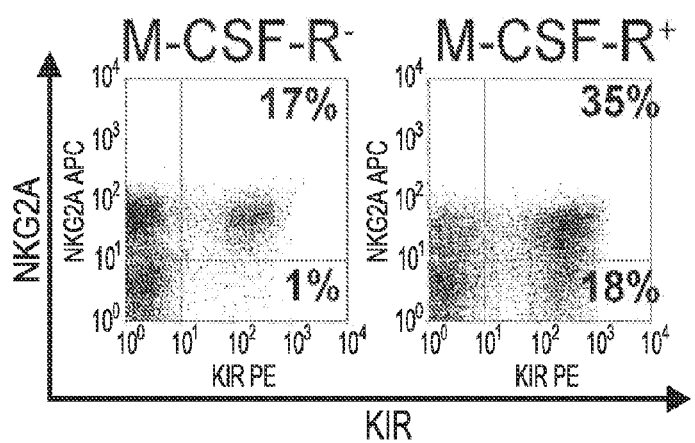
Figure 9D:
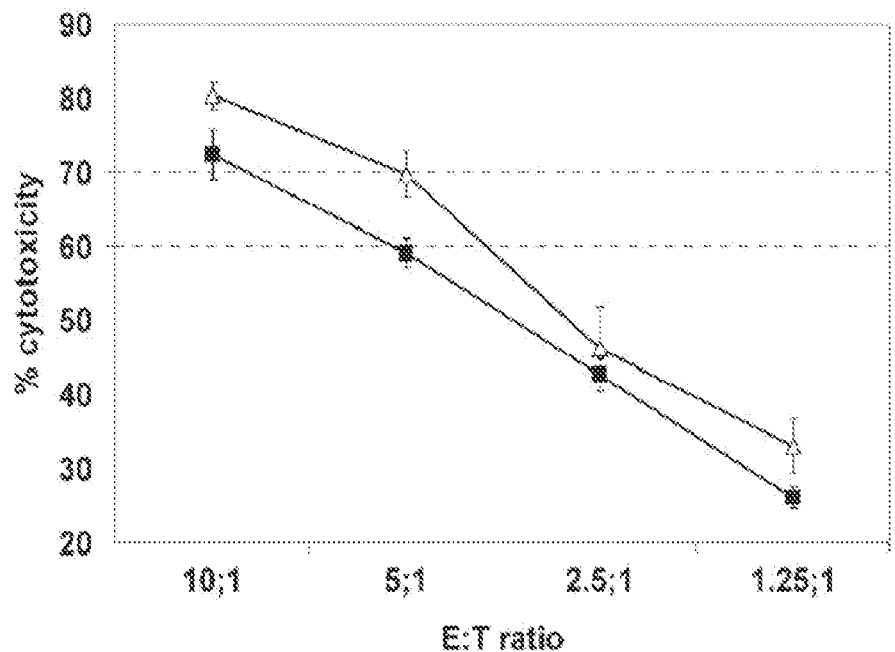
Figure 9E:
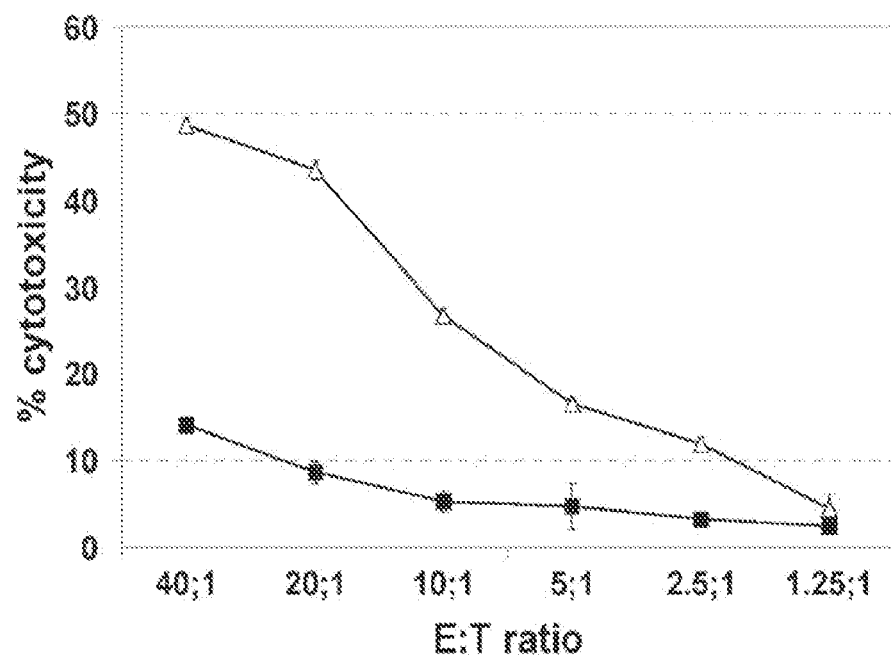

It was tested whether myeloid precursor-derived NK cells differ from the primarily lymphoid (M-CSFR)-fraction. Both CD56$^-$CD117$^+$M-CSFR$^+$ and CD56$^-$CD117$^+$M-CSFR subsets were cultured in conditions optimal for NK cell generation (cytokines, stroma and HDC). A higher percentage of NK cells derived from CD56$^-$CD117$^+$M-CSFR$^+$ progenitors expressed KIR compared to NK cells derived from CD56$^-$CD117$^+$M-CSFR precursors (FIGS. 9a and 7b, p<0.0001). Interestingly, NK cells derived from CD56$^-$ CD117$^+$M-CSFR$^+$ progenitors also contained a fraction of NK cells that were NKG2A$^-$KIR$^+$, while this fraction was absent in the CD56$^-$CD117$^+$M-CSFR$^-$ precursor derived NK cells (FIG. 9c) Both populations showed K562 killing, however M-CSFR$^+$ precursors consistently showed marginally higher cytotoxicity (FIG. 9d). HLA-deficient EBV transformed B cell targets (721.221) revealed a more pronounced difference. NK cells derived from M-CSFR-precursors showed minimal cytotoxicity while M-CSFR$^+$ derived cells readily killed these targets (FIG. 9e). There were not differences in perforin and granzyme B protein or in the expression activating receptors (2B4, NKp30, -46 and NKG2D) that would sufficiently explain these results (not shown). Thus, NK cells developing from distinct precursors have diverse phenotypic and functional properties.

Discussion

It is shown herein that a small fraction of CD34+ HPCs expressing any of the lineage markers previously associated with NK cell development (i.e., CD122, CD161, integrin β7 and CD45RA$^{high}$ and CD7)[13,16-18] can develop into NK cells under the influence of cytokines (IL-15, IL-7, SCF, FLT-3L and IL-3) and do not require HDC or stroma. However, most HPCs lack these markers (i.e., NKlin−) and are unable to differentiate into NK cells with these cytokines. Rather, NKlin− cells follow myeloid differentiation, as evidenced by surface markers (CD13, CD33, CD14, and CD1a) and intracellular enzymes (lysozyme, myeloperoxidase and macrosialyn (CD68)). These myeloid precursors could be recruited to the NK lineage by HDC and stroma. Perhaps not surprisingly, they gradually lost the ability to develop into NK cells as they progressed along myeloid differentiation (indicated by increasing CD13 staining). It was also shown that freshly isolated single CMPs and/or GMPs gave rise to NK cells under the influence of stroma and cytokines, but not cytokines alone. The observations that: (1) single CMP and GMP could generate NK cells, (2) myeloid cells coexisted with NK cells in cultures derived from a single CMP or GMP and (3) some granulocyte-macrophage colonies from these precursors (grown in methylocellulose) could subsequently differentiate into NK cells, provide solid evidence that myeloid precursors can give rise to NK cells. It was further shown that stroma and HDC mediate these properties, in part, through WNT activation. This is in agreement with the known role of TCF/LEF transcription factors in lymphocyte development and the ability of fetal liver stromal cells to trigger this pathway[31].

Myeloid precursors (CD56−CD117+M-CSFR+) arising in vitro were also isolated and their potential to generate NK cells was demonstrated. The observation that low concentrations of M-CSF induced CD14 expression by NK cells developing from myeloid precursors further supports the assertion that cells responding to M-CSF give rise to NK cells. These CD56+/−CD14+ cells appear to be NK cells (and not monocytes) since they fell in the lymphoid gate (by SSC vs. FSC) and expressed other NK antigens including CD94 and KIR (not shown). Higher doses of M-CSF, however, enforced monocytic differentiation, prohibiting NK cell development, suggesting a lineage choice between myeloid and NK cell fates. These choices are influenced by the environment (stroma) and growth factors (cytokines).

The results also indicate that myeloid precursor-derived NK cells have distinct properties. For instance, M-CSFR+ precursors, but not M-CSFR− counterparts require stroma or HDC for CD94 acquisition, a marker of maturation. Likewise, when these two starting populations are cultured with cytokines, stroma and HDC the resulting NK cells differ. Myeloid-derived NK cells show a significantly higher KIR expression, a KIR+NKG2A− cell fraction and higher cytotoxicity. KIR acquisition has been used as a measure of maturity[32], but the factors that lead to KIR expression are largely unknown. It was found that myc binds to KIR promoters, driving expression[33]. Interestingly, myc expression is linked to M-CSFR signaling and myeloid development[34]. Recently, a thymic pathway of NK cell development was demonstrated in rodents. Compared to the majority of NK cells, thymic-derived NK cells were uniquely dependent upon IL-7 and GATA-3 for development. The thymic-derived NK cells are characterized by low cytotoxicity, but high cytokine secretion potential[35]. These findings, along with the data presented here, support the concept, that various developmental trajectories, governed by specific transcription factors, influence the phenotypic and functional characteristics of the resulting population.

According to the widely accepted model of hematopoiesis, a multipotent HSC gives rise to CMPs or CLPs, committing the first choice in hematopoiesis between myeloid/erythroid and lymphoid fates. NK cells are believed to be exclusively derived from CLPs, which are, by definition, devoid of myeloid potential[8]. In disagreement with this, it is demonstrated herein that NK cells can be derived from freshly isolated CMPs, GMPs and CD34+CD64+ granulo-monocytic precursors[24] as well as CD33+CD13+, and M-CSFR+ progeny of cultured CD34+ HPC.

Whether this is unique to NK cells or extends to other lymphocyte subsets requires further investigation. However, neither T nor B cell differentiation occurred in the cultures (not shown). It is believed that CMP and GMP progenitors could give rise to other lymphocyte populations under appropriate, permissive conditions (DLL-1 expressing stroma and optimal cytokines for T cell development). In line with these observations, alternative models for lymphoid ontogeny have been proposed. Through the identification of common lympho-myeloid progenitors[5-6] and thymic T-cell progenitors that retain myeloid potential, it has been concluded that alternative schemes of hematopoietic lineage commitment should be considered[36-37]

We show that myeloid precursors can differentiate into NK cells and that under certain circumstances NK cells could be derived from seemingly restricted myeloid progenitors. Given the absence of NK cells in common γ-chain deficiency[40], myeloid precursors that develop into NK cells would conceivably acquire (and depend upon) this cytokine receptor for NK cell development.

In humans, two NK subsets can be distinguished, CD56$^{bright}$ and CD56$^{dim}$ [41]. The CD56$^{bright}$ subset has low cytotoxicity and readily produces cytokines in response to IL-12 and IL-18[42]. Only a small percentage of CD56$^{bright}$ cells show expression of KIR and CD16 but they do express c-kit receptor (CD117). In comparison, the CD56$^{dim}$ subset has higher cytotoxicity, abundant CD16 and KIR expression and lack CD117. The developmental relationship of the two subsets has not been unambiguously resolved. The vast majority of NK cells derived from in vitro from CD34+ HPC in this[20,22], as well as in other systems[12,19,21,43], resemble CD56$^{bright}$ NK cells. It is thus, noteworthy that NK cells derived from myeloid precursors are distinguished by higher cytotoxicity and KIR expression, as well a fraction of KIR expressing cells that lack NKG2A and lower levels of CD117 (not shown), features of the CD56$^{dim}$ subset.

Recently, it has been shown that dendritic cells (DCs) and NK cells share a common developmental progenitor[11], while others have described a rare CD14+ cell found in UCB (but not adult blood) that can give rise to NK cells under the influence of HDC, FLT-3L and IL-15[10]. These results are in line with the findings presented herein. It is posited herein that, similar to DCs[46], NK cells can have either a lymphoid or myeloid origin. The developmental relationship between NK cells and DC may be closer than previously recognized in that both can be derived from common precursors. Whether a stable cell type exists which constitutively shares the function of NK cells and dendritic cells[47-48] is a matter of debate[49-50]. Nevertheless in certain conditions DCs can acquire cytotoxicity, characteristic for NK cells[51]. Conversely NK cells can acquire antigen presenting ability[52]. The notion that myeloid precursors previously known to give rise to monocyte/macrophage and dendritic cells[53] are also capable of NK cell differentiation puts the recent findings in a new perspective[54]. In conclusion, NK cells can be derived from myeloid precursors.

Summary

As, since lymphoid progenitors can give rise to natural killer (NK) cells, NK ontogeny has been considered to be exclusively lymphoid. Herein it is demonstrated that human CD34+ hematopoietic progenitors (HPC) develop into NK cells in vitro in the presence of cytokines (IL-7, IL-15, SCF and FLT-3L). Adding hydrocortisone (HDC) and stromal cells greatly increases the frequency of progenitor cells that give rise to NK cells through the recruitment of myeloid precursors, including common myeloid progenitors (CMP) and granulocytic-monocytic precursors (GMP) to the NK cell lineage. Cells at more advanced stages of myeloid differentiation (with increasing expression of CD13, and M-CSFR+) could also differentiate into NK cells in the presence of cytokines, stroma and HDC. NK cells derived from myeloid precursors (CD56$^-$CD117$^+$M-CSF—R$^+$) showed more expression of killer Ig-like receptors (KIR), a fraction of KIR+ expressing cells that lacked NKG2A, a higher cytotoxicity compared to CD56$^-$CD117$^+$M-CSF—R$^-$ precursor derived NK cells and thus resemble the CD56$^{dim}$ subset of NK cells. Collectively, these studies show that NK cells can be derived from the myeloid lineage.

Bibliography
1. Weissman I L, et al. Annu Rev Cell Dev Biol. 2001; 17:387-403.
2. Orkin S H and Zon L I. Cell. 2008; 132:631-644.
3. Rothenberg E V. Immunity. 2007; 26:690-702.
4. Graft. Blood. 2002; 99:3089-3101.
5. Adolfsson J, et al. Cell. 2005; 121:295-306.
6. Katsura Y. Nat Rev Immunol. 2002; 2:127-132.
7. Ortaldo J R and Herberman R B. Annu Rev Immunol. 1984; 2:359-394.
8. Kondo M, et al. Cell. 1997; 91:661-672.
9. Colucci F, et al. Nat Rev Immunol. 2003; 3:413-425.
10. Perez S A, et al. Blood. 2003; 101:3444-3450.
11. Marquez C, et al. Blood. 1998; 91:2760-2771.
12. Lotzova E and Savary C A. Nat. Immun. 1993; 12:209-217.
13. Miller J S, et al. Blood. 1994; 83: 2594-2601.
14. Yu H, et al. Blood. 1998; 92:3647-3657.
15. Terstappen L W, et al. Blood. 1991; 77:1218-1227.
16. Rosmaraki E E, et al. Eur J. Immunol. 2001; 31:1900-1909.
17. Bennett I M, et al. J Exp Med. 1996; 184:1845-1856.
18. Freud A G, et al. Immunity. 2005; 22:295-304.
19. Sivori S, et al. Proc Natl Acad Sci USA. 2002; 99:4526-4531.
20. Miller J S and McCullar V. Blood. 2001; 98:705-713.
21. Briard D, et al. J. Immunol. 2002; 168:4326-4332.
22. Grzywacz B, et al. Blood. 2006; 108:3824-3833.
23. Freud A G, et al. J Exp Med. 2006; 203: 1033-1043.
24. Olweus J, et al. Blood. 1995; 85:2402-2413.
25. Manz M G, et al. Proc Natl Acad Sci USA. 2002; 99:11872-11877.
26. Bonnefoix T, et al. J Immunol Methods. 1996; 194:113-119.
27. Perez S A, et al. Blood. 2005; 106:158-166.
28. Rosenzwajg M, et al. Blood. 2000; 95:453-460.
29. Olweus J, et al. Blood. 1996; 88:3741-3754.
30. Sherr C J. Blood. 1990; 75:1-12.
31. Martin M A and Bhatia M. Stem Cells Dev. 2005; 14:493-504.
32. Freud A G and Caligiuri M A. Immunol Rev. 2006; 214:56-72.
33. Cichocki F, et al. Blood. 2009; 113:3245-3253.
34. Roussel M F, et al. Nature. 1991; 353:361-363.
35. Vosshenrich C A, et al. Nat. Immunol. 2006; 7: 1217-1224.
36. Wada H, et al. Nature. 2008; 452:768-772.
37. Bell J J and Bhandoola A. Nature. 2008; 452:764-767.
38. Metcalf D. Immunity. 2007; 26:669-673.
39. Purton L E and Scadden D T. Cell Stem Cell. 2007; 1:263-270.
40. Buckley R H, et al. J. Pediatr. 1997; 130:378-387.
41. Cooper M A, et al. Trends Immunol. 2001; 22:633-640.
42. Fehniger T A, et al. J. Immunol. 1999; 162:4511-4520.
43. Mrozek E, et al. Blood. 1996; 87:2632-2640.
44. Li H, et al. J Leukoc Biol. 1994; 56:117-123.
45. Sanchez M J, et al. J Exp Med. 1994; 180:569-576.
46. Wu L and Liu Y J. Immunity. 2007; 26:741-750.
47. Chan C W, et al. Nat. Med. 2006; 12:207-213.
48. Taieb J, et al. Nat. Med. 2006; 12:214-219.
49. Vosshenrich C A, et al. J Exp Med. 2007; 204:2569-2578.
50. Blasius A L, et al. J Exp Med. 2007; 204:2561-2568.
51. Stary G, et al. J Exp Med. 2007; 204:1441-1451.
52. Hanna J, et al. J Clin Invest. 2004; 114:1612-1623.
53. Fogg D K, et al. Science. 2006; 311:83-87.
54. Spits H and Lanier L L. Immunity. 2007; 26:11-16.

Example III

Generation of Innate Lymphoid Cells (ILCs) from Hematopoietic Stem Cells

Initial Method of Generating ILCs from Hematopoietic Stem Cells (HSCs)
1) In a 6 well plate, seed murine fetal stromal line EL.01D2 and grow to confluency.
2) Once confluent, irradiate to 3000 cGy.
3) In B0 media (MEM: Ham's F12 2:1, 10% human AB$^-$ sera) seed 15,000 CD34 cells (positively selected from umbilical cord blood, peripheral blood or bone marrow) into each of the 6 well plates.
4) Add the following cytokine: IL-3 (10 ng/ml), stem cell factor (20 ng/ml), FLT3L (10 ng/ml), IL7 (10 ng/ml), and IL-15 (10 ng/ml). Culture cells at 37 degrees 5% $CO_2$.
5) Change media every 3 to 7 days using demi-depletion, add fresh media containing the above cytokines (without IL-3).
6) At day 21, ~40% of the cells will have a stage III NKp phenotype (CD56$^{+/-}$CD117$^{high}$CD94$^-$, of which ~50% will be IL-22 secreting cells on the basis of CD7, CD94, and LFA1 negativity).

Generation of ILC Cells without IL-15
1) Follow steps 1-3 as above.
2) Culture CD34$^+$ cells in the above media containing IL-3, IL-7, SCF, FLT3L (at the above stated concentrations). Note: no IL-15.
3) Culture cells using the above technique (demi-depletion) for 42 days.
4) The resulting cell population will contain ~70% stage III NK progenitors marked by CD56$^{+/-}$CD117$^{high}$CD94$^-$, IL-22 producing cells will be marked by a CD7 CD94 and LFA1 negativity, as above.

Methods to Maintain Hematopoietic Progenitors in an ILC State

Maintain already established ILC cells (either from secondary lymphoid tissues or in vitro derived ILC cells (generated from CD34 cells) using biochemical agonists for the transcription factors aryl hydrocarbon receptor (AHR)

and/or the retinoic acid orphan receptor (ROR-γτ). Numerous AHR agonists and antagonists have been identified in the literature and can be used to maintain IL-22 producing cells using agonists and a reduction of ILC cells using the antagonists.

1) Purify ILC cells by any means.
2) Culture cells in BO media with agonists and media containing (IL7, stem cell factor, FLT3L+/−IL15)

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to produce IL-22 expressing Lymphoid Tissue Inducer-Like (LTi-like) NK22 cells comprising
    a) initially culturing CD34$^+$ cells in the presence of IL-3 and irradiated stroma;
    b) culturing the cells from a) in the presence of stem cell factor (SCF), FLT-3L, IL-7, IL-15 and irradiated stroma;
    c) culturing the cells from b) in the presence of IL-1β and IL-23, but in the absence of IL-7, so as to produce IL-22 expressing LTi-like NK22 cells.

2. The method of claim 1, wherein the CD34$^+$cells are seeded onto the stromal cell line.

3. The method of claim 1, wherein the CD34$^{30}$ cells are hematopoietic stem cells (HSCs).

4. The method of claim 1, wherein the CD34$^{30}$cells are isolated from umbilical cord blood.

5. The method of claim 1, wherein the cells are cultured for about 7 to about 40 days.

6. The method of claim 1, further comprising culturing the cells of a), b) and/or c) in the presence of hydrocortisone (HDC).

* * * * *

UNITED STATES PATENT AND TRADEMARK OFFICE
CERTIFICATE OF CORRECTION

PATENT NO. : 9,862,928 B2  
APPLICATION NO. : 13/991370  
DATED : January 9, 2018  
INVENTOR(S) : Verneris et al.

Page 1 of 2

It is certified that error appears in the above-identified patent and that said Letters Patent is hereby corrected as shown below:

In the Drawings

Sheet 17 of 24, Fig. 7B, delete "Nr of CD56+" and insert --No of $CD56^+$-- therefor.

In the Specification

Column 1, Line 14, after "reference.", insert --¶GOVERNMENT SUPPORT CLAUSE  
This invention was made with government support under HL055417 and CA111412 awarded by National Institutes of Health. The government has certain rights in the invention.--.

In Column 1, Line 30, delete "hematopoiesis"," and insert --hematopoiesis"[1],-- therefor.

In Column 1, Line 43, delete "discovery." and insert --discovery[7].-- therefor.

In Column 7, Line 28, delete "tonsilectomy" and insert --tonsillectomy-- therefor.

In Column 15, Line 43, delete "stern" and insert --stem-- therefor.

In Column 15, Line 47, delete "IL1" and insert --IL-1-- therefor.

In Column 16, Line 64, delete "1V" and insert --IV-- therefor.

In Column 17, Line 2, delete "1 μl," and insert --III,-- therefor.

In Column 17, Line 14, delete "1V" and insert --IV-- therefor.

In Column 19, Line 23, delete "(Stern" and insert --(Stem-- therefor.

In Column 19, Lines 33-34, delete "($10^-{_6}$M)." and insert --($10^{-6}$M).-- therefor.

Signed and Sealed this  
Nineteenth Day of March, 2019

Andrei Iancu  
*Director of the United States Patent and Trademark Office*

CERTIFICATE OF CORRECTION (continued)
U.S. Pat. No. 9,862,928 B2

In Column 19, Line 64, delete "M-CSFIce" and insert --M-CSFR$^+$-- therefor.

In Column 22, Line 66, delete "lyzozyme," and insert --lysozyme,-- therefor.

In Column 23, Line 42, delete "(CD56$^{+/-1\ CD}$117$^{high}$CD94$^-$)$^{18,22}$" and insert --(CD56$^{+/-}$CD117$^{high}$CD94$^-$)$^{18,22}$-- therefor.

In Column 24, Line 25, delete "M-CSFB$^-$" and insert --M-CSFR$^-$-- therefor.

In Column 24, Line 59, delete "(FIG. 9c)" and insert --(FIG. 9c).-- therefor.

In Column 26, Line 27, delete "considered$^{36-37}$" and insert --considered$^{36-37}$.-- therefor.

In Column 28, Line 37, delete "15,000" and insert --~15,000-- therefor.

In Column 29, Line 7, delete "BO" and insert --B0-- therefor.

In the Claims

In Column 31, Line 3, in Claim 1, after "comprising", insert --:--.

In Column 31, Line 12, in Claim 2, delete "CD34$^+$cells" and insert --CD34$^+$ cells-- therefor.

In Column 31, Line 14, in Claim 3, delete "CD34$^{30}$" and insert --CD34$^+$-- therefor.

In Column 31, Line 16, in Claim 4, delete "CD34$^{30}$cells" and insert --CD34$^+$ cells-- therefor.

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Synthetic primer

<400> SEQUENCE: 1
cccatcagct cccactgc                                                 18

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ggcaccacct cctgcatata                                               20

<210> SEQ ID NO 3
<211> LENGTH: 17
<212> TYPE: DNA
<213> ORGANISM: Artificial Sequence
<220> FEATURE:
<223> OTHER INFORMATION: Synthetic primer

<400> SEQUENCE: 3
gtcggagtca acggatt                                                  17

<210> SEQ ID NO 4
<211> LENGTH: 17
<212> TYPE: DNA
<213> ORGANISM: Artificial Sequence
<220> FEATURE:
<223> OTHER INFORMATION: Synthetic primer

<400> SEQUENCE: 4
aagcttcccg ttctcag                                                  17
```